(12) United States Patent
Selliah

(10) Patent No.: US 6,369,102 B2
(45) Date of Patent: *Apr. 9, 2002

(54) SUBSTITUTED TETRAHYDROFURAN ANALOGS OF PROSTAGLANDINS AS OCULAR HYPOTENSIVES

(75) Inventor: Robert D. Selliah, Fort Worth, TX (US)

(73) Assignee: Alcon Manufacturing, Ltd., Forth Worth, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/800,179

(22) Filed: Mar. 6, 2001

Related U.S. Application Data

(63) Continuation of application No. 09/440,248, filed on Nov. 15, 1999, now Pat. No. 6,197,812, which is a continuation of application No. 08/809,920, filed as application No. PCT/US96/17900 on Nov. 12, 1996, now Pat. No. 5,994,397.
(60) Provisional application No. 60/009,866, filed on Dec. 22, 1995.

(51) Int. Cl.$^7$ ................ A61K 31/341; C07D 307/12; C07D 307/14; C07D 307/20
(52) U.S. Cl. ................ 514/473; 549/475; 549/497; 549/499; 549/502; 549/504
(58) Field of Search ................ 514/473, 475, 514/497, 499, 502, 504

(56) References Cited

U.S. PATENT DOCUMENTS

| | | | |
|---|---|---|---|
| 3,883,659 A | 5/1975 | Vlattas | 424/285 |
| 4,088,779 A | 5/1978 | Vlattas | 424/285 |
| 4,133,817 A | 1/1979 | Lourens et al. | 260/340.9 P |
| 4,133,948 A | 1/1979 | Lourens et al. | 536/1 |
| 5,574,066 A | 11/1996 | Chan et al. | 514/548 |

FOREIGN PATENT DOCUMENTS

| | | |
|---|---|---|
| DE | 2460977 A | 7/1976 |
| DE | 2601333 A | 7/1976 |
| DE | 2618861 A | 11/1976 |
| DE | 2739277 A | 3/1978 |
| EP | 0667160 A2 | 8/1995 |
| EP | 0686628 A2 | 12/1995 |
| GB | 1458164 | 12/1976 |
| GB | 1539364 | 1/1979 |
| WO | WO 95/26729 | 10/1995 |

OTHER PUBLICATIONS

Alm, "The Potential of Prostaglandin Derivatives in Glaucoma Therapy" *Current Opinion in Ophthalmology* 4(II):44–50 (1993).

Arndt et al., "Stereospecific Synthesis of Modified Prostaglandins Derived from Carbohydrates. Part 1." *S. Afr. J. Chem.* 34(4):121–127 (Jun. 1981).

Giuffre, "The Effects of Prostaglandin $F_{2\alpha}$ in the Human Eye" *Graefe's Arch Clin Exp Ophthalmol* 222:139–141 (1985).

Hanessian et al., "Total Synthesis of 11–Oxaprostaglandin $F_{2\alpha}$ and $F_{2\beta}$" *Carbohydrate Research* 141:221–238 (1985).

Kerstetter et al., "Prostaglandin $F_{2\alpha}$–1–Isopropylester Lowers Intraocular Pressure Without Decreasing Aqueous Humor Flow" *American Journal of Ophthalmology* 105:30–34 (1988).

Lourens et al., "The Novel Stereospecific Synthesis of 11–Oxaprostaglandin $F_{2\alpha}$" *Tetrahedron Letters*, No. 43:3719–3722 Pergamon Press XP000644760 (1975).

Nakajima et al., "Effects of Prostaglandin $D_2$ and its Analogue, BW245C, on Intraocular Pressure in Humans" *Graefe'Arch Clin Exp Ophthalmol* 229:411–413 (1991).

Thiem et al., "Synthese von Oxaprostaglandinen aus 1,4:3,6–Dianhydro–D–sorbit" *Liebigs Ann. Chem.* 2151:2164 XP000644761 (1985).

Thierauch et al., "Prostaglandins and Their Receptors: II. Receptor Structure and Signal Transduction" *Journal of Hypertension* 12:1–5 (1994).

Verdoorn et al., "Synthesis of Methyl (5Z,13E)(15S)–9α–acetoxy–15–hydroxy–17–(3–trifluoromethylphenyl)–11–oxa–18,19,20–trinorprosta–5,13—dienoate" *S. Afr. Tydskr. Chem.* 40(2):134–138 (1987).

Vlattas et al., "Synthesis of 9–Oxaprostaglandins" *Tetrahedron Letters* No. 51/52:4455–4458, Pergamon Press, 1974.

Vlattas et al., "Synthesis of 11–Oxaprostaglandins" *Tetrahedron Letters* No. 51/52:4451–4454, XP000644759, Pergamon Press, 1974.

*Primary Examiner*—Ba K. Trinh
(74) *Attorney, Agent, or Firm*—Barry I. Copeland

(57) ABSTRACT

Substituted tetrahydrofuran analogs of prostaglandins and methods of their use in treating glaucoma and ocular hypertension are disclosed.

6 Claims, No Drawings

SUBSTITUTED TETRAHYDROFURAN ANALOGS OF PROSTAGLANDINS AS OCULAR HYPOTENSIVES

This application is a continuation of U.S. patent application Ser. No. 09/440,248 filed Nov. 15, 1999, now U.S. Pat. No. 6,197,812, which is a continuation of U.S. patent application Ser. No. 08/809,920 filed Apr. 4, 1997, a national application under 37 U.S.C. §371 of PCT application Serial No. PCT/US 96/17900 filed Nov. 12, 1996, now U.S. Pat. No. 5,994,397, which draws priority from U.S. Provisional Application Serial No. 60/009,866 filed Dec. 22, 1995 (now abandoned).

BACKGROUND OF THE INVENTION

The present invention relates to novel compounds and compositions, and methods of their use in the treatment of glaucoma and ocular hypertension. In particular, the present invention relates to the use of certain substituted tetrahydrofuran analogs of D and F series prostaglandins to treat glaucoma and ocular hypertension.

Glaucoma is a progressive disease which leads to optic nerve damage, and, ultimately, total loss of vision. The causes of this disease have been the subject of extensive studies for many years, but are still not fully understood. The principal symptom of and/or risk factor for the disease is elevated intraocular pressure or ocular hypertension due to excess aqueous humor in the anterior chamber of the eye.

The causes of aqueous humor accumulation in the anterior chamber are not fully understood. It is known that elevated intraocular pressure ("IOP") can be at least partially controlled by administering drugs which reduce either the production of aqueous humor within the eye, such as beta-blockers and carbonic anhydrase inhibitors, or increase the flow of aqueous humor out of the eye, such as miotics and sympathomimetics.

Most types of drugs conventionally used to treat glaucoma have potentially serious side effects. Miotics such as pilocarpine can cause blurring of vision and other visual side effects, which may lead either to decreased patient compliance or to termination of therapy. Systemically administered carbonic anhydrase inhibitors can also cause serious side effects, such as nausea, dyspepsia, fatigue, and metabolic acidosis, which side effects can affect patient compliance and/or necessitate the termination of treatment. Moreover, some beta-blockers have increasingly become associated with serious pulmonary side effects attributable to their effects on beta-2 receptors in pulmonary tissue. Sympathomimetics may cause tachycardia, arrhythmia and hypertension. There is therefore a continuing need for therapies which control the elevated intraocular pressure associated with glaucoma.

Prostaglandins, which are metabolite derivatives of arachidonic acid, have recently been pursued for possible efficacy in lowering IOP. Arachidonic acid in the body is converted to prostaglandin $G_2$, which is subsequently converted to prostaglandin $H_2$. Other naturally occurring prostaglandins are derivatives of prostaglandin $H_2$. A number of different types of prostaglandins have been discovered including A, B, D, E, F, G, I and J-series prostaglandins (EP 0 561 073 A1). Of interest in the present invention are compounds which are believed to exhibit IOP lowering mechanisms similar to those exhibited by $PGD_2$ (formula (I)) and $PGF_{2\alpha}$ (formula (II)):

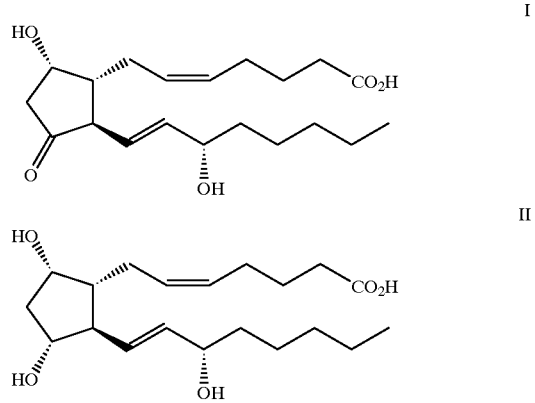

The relationship between prostaglandin DP receptor activation and IOP lowering effects is not well understood. Various publications have reported that DP receptor activation leads to second messenger activation and in particular, to the stimulation of adenylate cyclase and resultant increases in cAMP levels (Thierauch, Prostaglandins and their Receptors: II. Receptor Structure and Signal Transduction, *Journal of Hypertension*, volume 12, pages 1–5 (1994). Regardless of mechanism, $PGD_2$ has been shown to lower IOP (Nakajima, Effects of Prostaglandin $D_2$ and its analog, BW245C, on Intraocular Pressure in Humans, *Graefe's Archive Ophthalmology*, volume 229, pages 411–413 (1991)). Thus, it has been of interest in the field to develop synthetic $PGD_2$ analogs with IOP lowering efficacy.

Synthetic $PGD_2$-type analogs have been pursued in the art (*Graefe's Archive Ophthalmology*, volume 229, pages 411–413 (1991)). Though some $PGD_2$-type molecules lower IOP, these types of molecules have also been associated with undesirable side effects resulting from topical ophthalmic dosing. Such effects have included an initial increase in IOP, conjunctival hyperemia, increases in microvascular permeability, and increases in eosinophile infiltration (Alm, The Potential of Prostaglandin Derivatives in Glaucoma Therapy, *Current Opinion in Ophthalmology*, volume 4, No. 11, pages 44–50 (1993)).

Similarly, the relationship of prostaglandin FP receptor activation and IOP lowering effects is not well understood. It is believed that FP receptor activation leads to increased outflow of aqueous humor. Regardless of mechanism, $PGF_{2\alpha}$, and some of its analogs have been shown to lower IOP (Giuffre, The Effects of Prostaglandin $F_{2\alpha}$, the Human Eye, *Graefe's Archive Ophthalmology*, volume 222, pages 139–141 (1985); and Kerstetter et al., Prostaglandin $F_{2\alpha}$-1-Isopropylester Lowers Intraocular Pressure Without Decreasing Aqueous Humor Flow, *American Journal of Ophthalmology*, volume 105, pages 30–34 (1988)). Thus, it has been of interest in the field to develop synthetic $PGF_{2\alpha}$ analogs with IOP lowering efficacy.

Synthetic $PGF_{2\alpha}$-type analogs have been pursued in the art (*Graefe's Archive Ophthalmology*, volume 229, pages 411–413 (1991)). Though $PGF_{2\alpha}$-type molecules may lower IOP, these types of molecules have also been associated with undesirable side effects resulting from topical ophthalmic dosing. Such effects include an initial increase in IOP, breakdown of the blood aqueous barrier and conjunctival hyperemia (Alm, The Potential of Prostaglandin Derivatives in Glaucoma Therapy, *Current Opinion in Ophthalmology*, volume 4, No.11, pages 44–50 (1993)).

Based on the foregoing, a need exists for the development of molecules that may activate the prostaglandin DP and/or FP receptors, yielding a more efficacious lowering of IOP, while exhibiting fewer or reduced side effects.

An agent which exhibits comparable or improved efficacy, but with reduced side effects when compared to other agents, is said to have an improved therapeutic profile. It is an object of this invention to provide a class of IOP lowering agents with an improved therapeutic profile over endogenous prostaglandins, and methods of their use.

SUMMARY OF THE INVENTION

The present invention is directed to compositions and methods of their use in treating glaucoma and ocular hypertension. In particular, the present invention provides certain classes of substituted tetrahydrofurans which may possess functional DP and/or FP receptor agonist activity, and methods of their use in treating glaucoma and ocular hypertension.

DETAILED DESCRIPTION OF THE INVENTION

It has unexpectedly been found that substituted tetrahydrofurans of the present invention exhibit an improved therapeutic profile in the treatment of glaucoma and ocular hypertension when compared to natural prostaglandins and many of their known analogs. The substituted tetrahydrofurans of the present invention are heptanoic acid derivatives having the following formula (III):

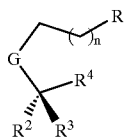
(III)

wherein:

R=pharmaceutically acceptable ester moiety, $CO_2R^1$, $CONR^7R^8$, $CH_2OR^9$, or $CH_2NR^{10}R^{11}$, where $R^1$=H or cationic salt moiety; $R^7$ and $R^8$ are the same or different=H or alkyl; $R^9$=H, acyl, or alkyl; and $R^{10}$ and $R^{11}$ are the same or different=H, acyl, or alkyl; with the proviso that if one of $R^{10}$ and $R^{11}$=acyl, then the other=H or alkyl;

n=0 or 2;

G is:

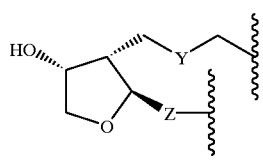
(i)

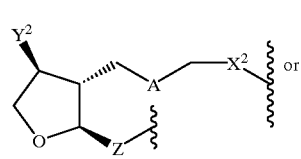
(ii)

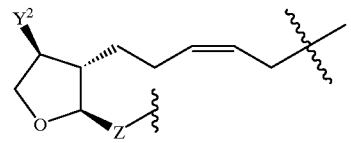
(iii)

wherein:

Y=$CH_2CH$=$CH$ (cis olefin), $CH$=$CHCH_2$ (cis olefin), or $CH_2CH_2CH_2$;

Z=C≡C, trans CH=CH, or $CH_2CH_2$;

$Y^2$=halogen or alkoxy;

$X^2$=O, S, or $CH_2$; and

A=cis CH=CH, $CH_2CH_2$, or C≡C;

one of $R^2$ and $R^3$=H, and the other=F or OH, where the OH may be free or functionally modified; or $R^2$ and $R^3$ taken together=$OCH_2CH_2O$ or double bonded O (carbonyl); and $R^4$=cyclohexyl, linear or branched $C_5$–$C_7$ alkyl, or $R^5$, wherein:

$R^5$=$(CH_2)_m$Xphenyl or $(CH_2)_p$ $Z^2$, where X=O or $CH_2$; m=1–6; the phenyl is either unsubstituted or substituted with $R^6$, where $R^6$=halogen, $CH_3$, $CF_3$, CN, $OCH_3$ or acetyl; p=0–6; and $Z^2$ = 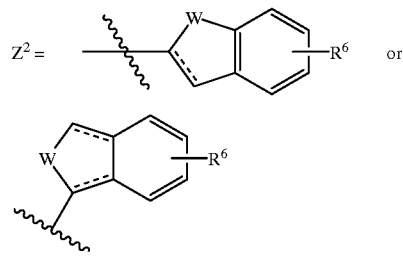 or

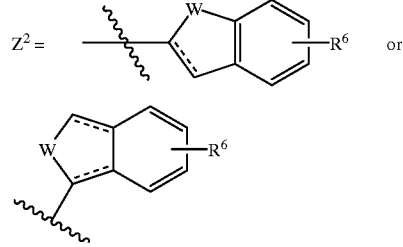

wherein:

W=O, $CH_2$, $CH_2CH_2$, or CH=CH; and $R^6$ is as defined above;

provided that when G is (i) then $R^4$=$R^5$, and when G is (ii) or (iii) then $R^4$=cyclohexyl, linear or branched $C_5$–$C_7$ alkyl, and $R^2$, $R^3$ are different=H and OH.

For purposes of the foregoing and following definitions, the term "pharmaceutically acceptable ester moiety" means any ester moiety that would be suitable for therapeutic administration to a patient by any conventional means without significant deleterious health consequences. Similarly, the term "ophthalmically acceptable ester moiety" means any pharmaceutically acceptable ester moiety that would be suitable for ophthalmic application, i.e. non-toxic and non-irritating. Preferred are ophthalmically acceptable esters such as alkyl and alkylcycloalkyl esters of carboxylic acids. Most preferred are $C_2$–$C_5$ alkyl esters of carboxylic acids, and especially isopropyl esters.

Preferred compounds of the present invention are those of formula IV:

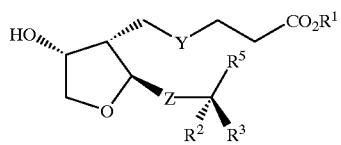

(IV)

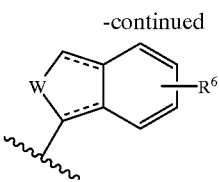

wherein:

W=O, CH$_2$, CH$_2$CH$_2$, or CH=CH; and R$^6$ is as defined above.

Other preferred compounds of this invention include those of formula V:

(V)

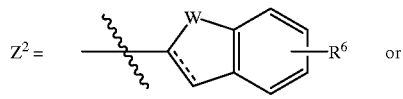

wherein:

R$^1$=H or C$_2$–C$_5$ linear or branched alkyl;

X$^2$=O, or CH$_2$;

A =cis CH=CH, CH$_2$CH$_2$, or C≡C;

Y$^2$=halogen;

Z=C≡C, trans CH=CH, or CH$_2$CH$_2$;

R$^2$, R$^3$ are different=H, and OH; and

R$^4$=cyclohexyl, or C$_5$–C$_7$ linear or branched alkyl.

Especially preferred compounds of this invention are:

wherein:

R$^1$=H, or C$_2$–C$_5$ linear or branched alkyl;

Y=CH$_2$CH=CH (cis olefin), CH=CHCH$_2$ (cis olefin), or CH$_2$CH$_2$CH$_2$;

Z=C≡C, trans CH=CH, or CH$_2$CH$_2$;

one of R$^2$ and R$^3$=H, and the other=F or OH, where the OH may be free or functionally modified; or R$^2$ and R$^3$ taken together=OCH$_2$CH$_2$O or double bonded O (carbonyl); and R$^5$=(CH$_2$)$_m$Xphenyl or (CH$_2$)$_p$ Z$^2$, where X=O or CH$_2$; m=1–6; the phenyl is either unsubstituted or substituted with R$^6$, where R$^6$=halogen, CH$_3$, CF$_3$, CN, OCH$_3$ or acetyl; p=0–6; and

Z$^2$=

Z$^2$ = 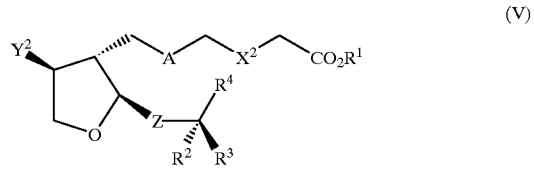 or

| Compound Number | Compound Name | Compound Structure |
|---|---|---|
| VI | Isopropyl [2R(1E,3R),3S(5Z),4R]-7-[Tetrahydro-2-[4-(3-chlorophenoxy)-3-hydroxy-1-butenyl]-4-hydroxy-3-furanyl]-5-heptenoate. | 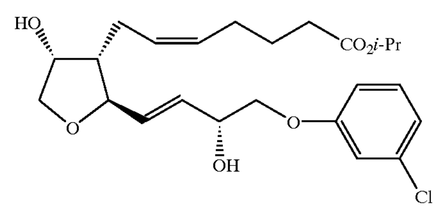 |
| VII | Isopropyl [2R(1E,3S),3R(5Z),4S]-7-[Tetrahydro-4-chloro-2-(3-cyclohexyl-3-hydroxy-1-propenyl)-3-furanyl]-3-oxa-5-heptenoate. | 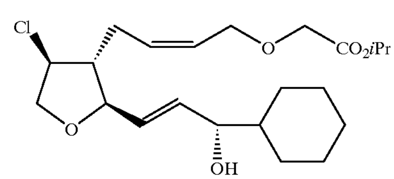 |
| VIII | Isopropyl [2R(1E,3R),3S(4Z),4R]-7-[Tetrahydro-2-[4-(3-chlorophenoxy)-3-hydroxy-1-butenyl]-4-hydroxy-3-furanyl]-4-heptenoate. | 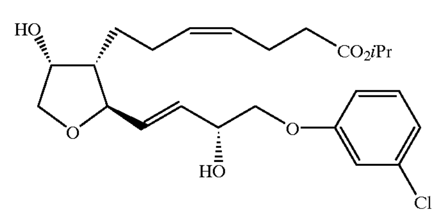 |

-continued

| Compound Number | Compound Name | Compound Structure |
|---|---|---|
| IX | Isopropyl [2S(3S),3R(5Z),4S]-7-[Tetrahydro-4-chloro-2-(3-cyclohexyl-3-hydroxy-1-propynyl)-3-furanyl]-3-oxa-5-heptenoate. | 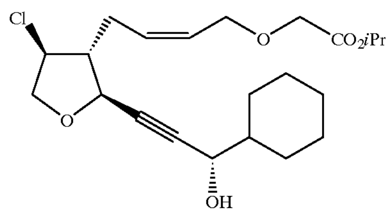 |

The PGD$_2$ type analogs of the present invention (i.e. Compound III, wherein G is (ii) or (iii)) are believed to be novel.

With the exception of: methyl (5Z,13E,15R)-9α-acetoxy-15-hydroxy-17-(3-trifluoromethylphenyl)-11-oxa-18,19,20-trinorprosta-5,13-dienoate and methyl (5Z,13E,15S)-9α-acetoxy-15-hydroxy-17-(3-trifluoromethylphenyl)-11-oxa-18,19,20-trinorprosta-5,13-dienoate, syntheses of which have been reported by Verdoorn, et al., *S. African J. Chem.*, 40:134–138 (1987), the PGF$_{2α}$-type analogs useful in the present invention (i.e. Compound III, wherein G is (i)) are also believed to be novel. Related 11-oxa PGFs outside the scope of the present invention are, however, known and their syntheses are described in the literature. The 11-oxa analogs of PGF$_{2α}$ and PGF$_{2β}$ are disclosed in Hanessian, et al., *Carbohydrate Research*, 141:221–238 (1985); and Thiem et al., *Liebigs Ann. Chem.*, 2151–2164 (1985). Arndt, et al., *S. African J. Chem.*, 34:121–127 (1981), and U.S. Pat. No. 4,133,817, similarly disclose 11-oxa analogs of PGF$_{2α}$. The entire contents of these references are hereby incorporated herein.

In the foregoing illustrations, as well as those provided hereinafter, wavy line attachments indicate that the configuration may be either alpha (α) or beta (β). The dashed lines on bonds between carbons, e.g. in the bicyclic structural formula for Z$^2$, indicate a single or double bond. Two solid lines present between carbons specify the configuration of the relevant double bond. Hatched lines indicate the α configuration, and a solid triangular line indicates the β configuration.

In the following Examples 1–8, the following standard abbreviations are used: g=grams (mg=milligrams); mol=moles (mmol=millimoles); mL=milliliters; mm Hg=millimeters of mercury; mp=melting point; bp=boiling point; h=hours; and min=minutes. In addition, "NMR" refers to nuclear magnetic resonance spectroscopy and "MS" refers to mass spectrometry.

EXAMPLE 1

Synthesis of (3aR, 4S, 6aR)-Hexahydro-2-Oxofuro-[3,4-b]Furan-4-Carboxaldehyde (11)

The compounds of this invention (both the PGD$_2$-type and the PGF$_{2α}$-type analogs) may be prepared from the same intermediate compound, (3aR, 4S, 6aR)-hexahydro-2-oxofuro[3,4-b]furan-4-carboxaldehyde (11) which is prepared from the readily available 1,2-O-isopropylidene-α-D-xylofuranose (1) according to published methodology (Arndt, et al. *S. Afr. J. Chem.*, 34:121–127 (1981); U.S. Pat. No. 4,133,948). The following Scheme 1 outlines the synthetic route to (11).

Scheme 1:
Synthesis of Aldehyde 11

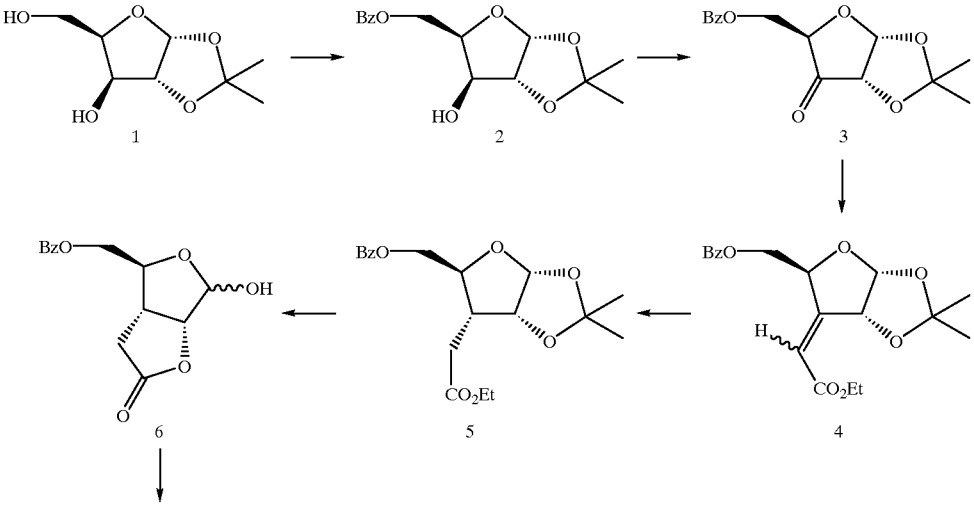

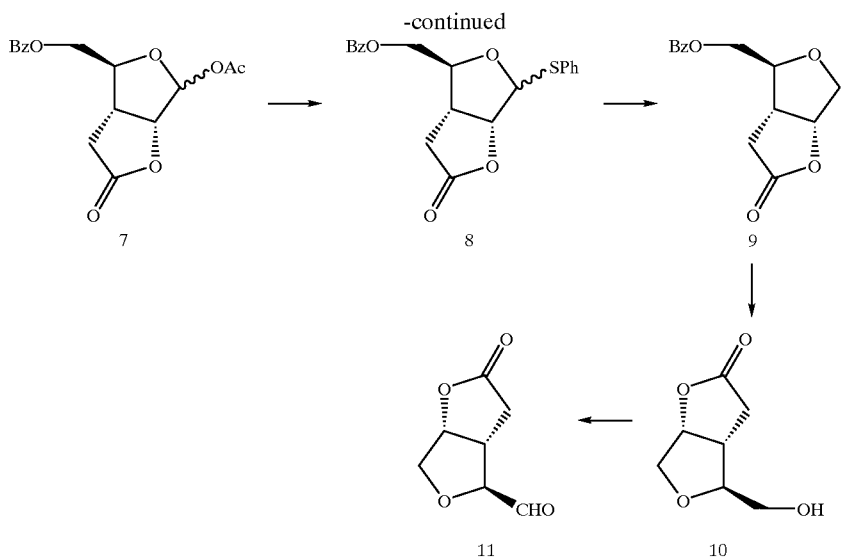

A: 5-O-Benzoyl-1,2-O-Isopropylidene-α-D-Xylofuranose (2):

A solution of 1,2-O-isopropylidene-α-D-xylofuranose 1 (30 g, 0.15 mol) in 360 mL of $CH_2Cl_2$ was cooled to 0° C. and to it was added 20 mL (0.23 mol) of pyridine and a catalytic amount (1.0 g) of N,N-dimethylaminopyridine. The resulting mixture was stirred at 0° C. for 10 min, at which time 20 mL (0.17 mol) benzoyl chloride was added to it dropwise over a period of 30 min. The reaction mixture was stirred at 0° C. for an additional 30 min and then quenched by the addition of 200 mL a saturated solution of $NH_4Cl$. The reaction was allowed to warm to room temperature, the layers were separated, and the aqueous layer was extracted with 3×50 mL of $CH_2Cl_2$. The combined organic extracts were washed with 3×50 mL of a 10% aqueous solution of $CuSO_4$, 2×50 mL of water and brine. The organic solution was dried over anhydrous $MgSO_4$, filtered and concentrated. The crude product mixture was purified by chromatography on silica gel to afford 44.3 g (95% yield) of 2 as a colorless liquid: $R_f$ 0.54 (60% EtOAc/hexane); $^1$H-NMR ($CDCl_3$) δ 8.03 (m, 2H), 7.40–7.68 (m, 3H), 5.97 (d, 1H, J=3.6 Hz), 4.80 (m, 1H), 4.61 (d, 1H, J=3.4 Hz), 4.37 (m, 2H), 4.20 (s, broad, 1H), 3.35 (broad, 1H), 1.50 (s, 3H), 1.32 (s, 3H).

B: 5-O-Benzoyl-1,2-O-Isopropylidene-α-D-Erythropentofuranos-3-Ulose (3):

A solution of oxalyl chloride (2.0 M in $CH_2Cl_2$, 113 mL, 0.22 mol) in 400 mL of anhydrous $CH_2Cl_2$ was cooled to −78° C. under a $N_2$ atmosphere. To this, a solution of dimethylsulfoxide (32 mL, 0.45 mol) in 50 mL of anhydrous $CH_2Cl_2$ was added dropwise over a period of 5 min. After the resulting solution had been stirred at the same temperature for 5 min, a solution of 2 (44.3 g, 0.15 mol) in 500 mL of anhydrous $CH_2Cl_2$ was added to it dropwise over a period of 15 min. Stirring was continued at −78° C. for an additional 15 min. Triethylamine (60 mL, 0.42 mol) was then added to the reaction mixture, and after a further 15 min at −78° C. the cold temperature bath was removed, and the stirring was continued for 10 min. The reaction was then quenched by the addition of 400 mL of water. The biphasic mixture was allowed to warm to room temperature and the layers were separated. The aqueous layer was extracted with 3×100 mL of $CH_2Cl_2$. The organic extracts were combined and washed with water (3×100 mL) and brine and was dried over anhydrous $Na_2SO_4$. Filtration and solvent removal afforded crude 3 (42.5 g, 96% yield) as a pale yellow solid, which was used in the next step without further purification: $^1$H-NMR ($CDCl_3$) δ 7.97 (m, 2H), 7.40–7.65 (m, 3H), 6.14 (d, 1H, J=4.40 Hz), 4.69 (m, 2H), 4.44 (m, 2H), 1.15 (s, 3H), 1.43 (s, 3H).

C: (3aR, 4S, 6RS, 6aR)-4-(Benzoyloxy)Methylhexahydro-6-Hydroxyfuro[3,4-b]Furan-2-One (6):

The crude sample of 3 (42.5 g, 0.15 mol), triethylphosphonoacetate (40.5 g, 0.18 mol) and lithium chloride (7.6 g, 0.18 mol) were combined and dissolved in 1.0 L of anhydrous THF. The solution was cooled to 0° C. and to it triethylamine (25.3 mL, 0.18 mol) was added dropwise. The resulting slurry was allowed to warm to room temperature gradually, and stirred under a $N_2$ atmosphere for 24 h. The reaction mixture was then poured into 500 mL of a 50% aqueous NaCl solution. The layers were separated and the aqueous layer was extracted with 2×200 mL of EtOAc. The combined organic extracts were dried over anhydrous $MgSO_4$. Filtration and solvent removal afforded 50 g of the crude enoate 4 as a mixture of two diastereomers which was used in the next step: $R_f$ 0.58 and 0.50 (minor and major isomers, respectively, 50% EtOAc/hexane).

To a suspension of 30–40 g of Raney-Ni (Aldrich, washed to neutrality with distilled water) in 750 mL of methanol the crude enoate 4 (50 g) from above was added, and the resulting mixture was hydrogenated at 65–70 psi, at room temperature in a Parr high-pressure reactor for 18 h. The reaction mixture was carefully filtered through a pad of celite. The solids were washed thoroughly with methanol. The filtrates were combined and evaporated, and the crude product mixture was purified by passage through a short pad of silica gel to afford 46.7 g (85% yield for two steps) of 5 as a colorless liquid. This material was carried onto the next step: $R_f$ 0.46 (50% EtOAc/hexane); $^1$H NMR ($CDCl_3$) δ 8.03 (m, 2H), 7.40–7.65 (m, 3H), 5.88 (d, J=3.6 Hz, 1H), 4.85 (m, 1H), 4.05–4.65 (m, 5H), 2.78 (m, 1H), 2.40 (m, 2H), 1.52 (s, 3H), 1.32 (s, 3H), 1.25 (t, J=7.15 Hz, 3H).

The acetonide 5 (46.7 g, 0.12 mol) obtained above was dissolved in 250 mL of a 4:1 mixture of glacial acetic acid and water, and the resulting solution was heated at 100° C. for 3.5 h. The reaction mixture was cooled to room temperature and the solvent was removed in vacuo. The residue was dissolved in 100 mL of toluene and the solution was concentrated to afford 39.6 g (quantitative yield) of 6 as pale yellow viscous liquid: $R_f$ 0.23 (50% EtOAc/hexane); $^1$H-NMR (CDCl$_3$) δ 8.01 (m, 2H), 7.38–7.69 (m, 3H), 5.62 (s, 1H), 4.93 (d, 1H, J=6.02 Hz), 4.30–4.70 (m, 3H), 3.20 (m, 1H), 2.50–3.05 (m, 2H).

D:(3aR, 4S, 6RS, 6aR)-6-Acetyloxy-4-(Benzoyloxy) Methylhexahydrofuro[3,4-b]Furan-2-One (7):

The lactone 6 (39.6 g, 0.14 mol) was dissolved in 70 mL of pyridine. To this solution 70 mL of acetic anhydride was added and the resulting mixture was stirred at room temperature for 20 h. The solvent was then evaporated and the residue was dissolved in 1.5 L of EtOAc. This solution was sequentially washed with 2×150 mL of water, 3×150 mL of a 0.25 N HCl solution water, 1×150 mL water and 1×100 mL brine. The organic layer was dried over anhydrous MgSO$_4$, filtered and concentrated. The crude product was isolated as a yellow solid which was titurated with hot ether to afford 29.0 g of a white crystalline solid which was found to be a single diastereomer of the acetate by $^1$H-NMR. The mother liquor was concentrated and purified by chromatography on silica gel to afford 6.7 g of a mixture of diastereomeric acetates as a yellow liquid. The combined yield of 7 being 87%: $R_f$ 0.3 (60% EtOAc/hexane); $^1$H-NMR (CDCl$_3$) δ (for major isomer only) 8.03 (m, 2H), 7.42–7.68 (m, 3H), 6.41 (s, 1H), 5.01 (d, 1H, J=6.3 Hz), 4.45 (s, broad, 3H), 3.22 (m, 1H), 2.90 (dd, 1H, J=14.4, 9.0 Hz), 2.62 (dd, 1H, J=14.4, 3.4 Hz), 2.03 (s, 3H).

E:(3aR, 4S, 6RS, 6aR)-4-(Benzoyloxy)Methylhexahydro-6-Phenylthiofuro[3,4-b]Furan-2-One (8):

To a suspension of 7 (35.7 g, 0.11 mol) and thiophenol (14.8 mL, 0.13 mol) in 220 mL of a 4:1 mixture of anhydrous toluene and dichloromethane at room temperature, boron trifluoride etherate (6.9 mL, 0.05 mol) was added dropwise. The resulting mixture was stirred at the same temperature for 6.5 h and then carefully poured into a biphasic mixture of 1000 mL of EtOAc and 100 mL of a saturated aqueous solution of NaHCO$_3$ (sat. NaHCO$_3$). The layers were separated and the organic layer was washed with 2×100 mL of saturated NaHCO$_3$, 100 mL of water and 100 mL of brine. The organic layer was dried over anhydrous MgSO$_4$, filtered and concentrated to afford a yellow liquid. This material was dissolved in 50 mL of CHCl$_3$, and to it was added 200 mL of ether and 50 mL of hexane. The resulting solution was briefly cooled to −78° C. to induce crystallization. White powdery solid formed which was filtered off and washed with cold ether to afford 29.6 g of 8 (72% yield) as a mixture of two diastereomers: $R_f$ 0.70 and 0.53 (minor and major isomers, respectively, 60% EtOAc/hexane); $^1$H-NMR (CDCl$_3$) δ (for major isomer only) 8.01 (m, 2H), 7.42–7.70 (m, 5H), 7.27 (m, 3H), 5.89 (d, 1H, J=5.2 Hz), 5.29 (dd, 1H, J=7.7, 5.2 Hz), 4.55 (m, 2H), 4.48 (m, 1H), 2.60–3.12 (m, 3H).

F:(3aR, 4S, 6aR)-4-(Bezoyloxy)Methylhexahydrofuro[3,4-b]Furan-2-One (9):

A 3-neck, 1000 mL round-bottom flask, equipped for overhead mechanical stirring, was charged with 29.6 g of 8 (80 mmol), 500 mL of ethanol and approximately 30 g of Raney-Ni (Aldrich, which had been washed to neutrality with distilled water). The resulting slurry was heated at reflux for 5 h while stirring vigorously. The reaction mixture was then cooled to room temperature, and the solids were carefully filtered off through a pad of celite. The residue was washed thoroughly with ethanol, and the combined filtrates were concentrated to afford a yellow solid which was purified by chromatography on silica gel to afford 7.63 g (36% yield) of 9 as a white solid. A small sample was recrystallized from acetone/hexane to afford colorless needles: mp 89.5–90.0° C.; $[α]_D^{22}$+3.18 (c=0.8 in CHCl$_3$); $R_f$ 0.36 (60% EtOAc/hexane); $^1$H-NMR (CDCl$_3$) δ 8.01 (m, 2H), 7.40–7.65 (m, 3H), 5.15 (m, 1H), 4.41 (m, 2H), 4.05–4.32 (m, 3H), 2.80–3.05 (m, 2H), 2.56 (d, 1H, J=15.7 Hz); MS m/z at 263 for (M+H)$^+$.

G:(3aR, 4S, 6aR)-Hexahydro-2-Oxofuro[3,4-b]Furan-4-Carboxaldehyde (11):

To a solution of the benzoate 9 (2.63 g, 10.0 mmol) in 50 mL of warm methanol was added 1.4 g (10.0 mmol) of solid K$_2$CO$_3$. The resulting slurry was stirred at room temperature for 2.5 h, at which time 150 mL of water was added and the mixture was treated with Amberlyst-15 (purified and activated) until the solution was at pH 2–3. The resin was filtered and washed with 50 mL of water, and the filtrates were combined and concentrated to approximately 200 mL. This solution was extracted with 3×50 mL of EtOAc, the organic extracts were discarded and the aqueous phase was evaporated in vacuo. The residue was taken up in 50 mL of toluene and the solvent was evaporated; this drying procedure was repeated twice. The product hydroxylactone 10 thus obtained (1.64 g, 95% yield) was isolated as a pale yellow liquid. This material was used without further purification: $^1$H-NMR (d$_6$-DMSO) δ (crude sample) 5.12 (m, 1H), 4.81 (t, 1H, J=5.6 Hz, OH), 3.98 (dd, 1H, J=10.3, 4.1 Hz), 3.85 (d, 1H, J=10.5 Hz), 3.75 (m, 1H), 3.44 (m, 2H), 2.85 (m, 2H), 2.48 (m, 1H).

A solution of oxalyl chloride (2.0 M in CH$_2$Cl$_2$, 5.4 mL, 10.8 mmol) in 25 mL anhydrous CH$_2$Cl$_2$ was cooled to −78° C. under a N$_2$ atmosphere. To this, a solution of DMSO (1.5 mL, 21.6 mmol) in 5.0 mL of CH$_2$Cl$_2$ was added dropwise. The resulting mixture was stirred for 5 min, and then a solution of the hydroxylactone 10 obtained above (1.14 g, 7.21 mmol) in 50 mL of anhydrous CH$_2$Cl$_2$ was added dropwise. After 15 min at −78° C., triethylamine (2.85 mL, 20.2 mmol) was added to the reaction and stirring was continued for an additional 15 min at −78° C. The reaction was then allowed to warm to room temperature and filtered through a pad of celite. The filter cake was washed with CH$_2$Cl$_2$, the filtrates were combined and concentrated to approximately 10 mL; this solution was applied to a column of silica gel for chromatographic purification. The aldehyde 11 (0.9 g, 80% yield) was isolated as a colorless liquid: $R_f$ 0.6 (acetone); $^1$H-NMR (CDCl$_3$) δ 9.71 (s, 1H), 5.10 (m, 1H), 4.24 (m, 1H), 3.65–3.89 (m, 2H), 2.96 (m, 1H), 2.64 (m, 1H), 1.85 (m, 1H).

EXAMPLE 2

Synthesis of Isopropyl [2R(1E,3R),3S(5Z),4R]-7-[Tetrahydro-2-[4-(3-Chlorophenoxy)-3-Hydroxy-1-Butenyl]-4-Hydroxy-3-Furanyl]-5-Heptenoate (VI)

Compound VI may be prepared according to the method described by the following Scheme 2.

Scheme 2:
Synthesis of Compound VI:

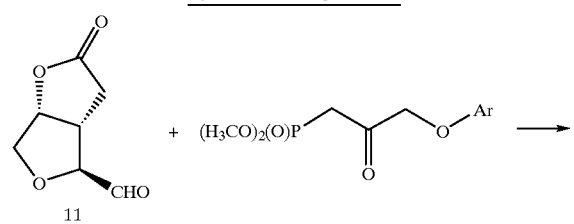

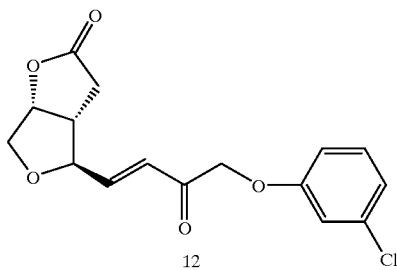

12

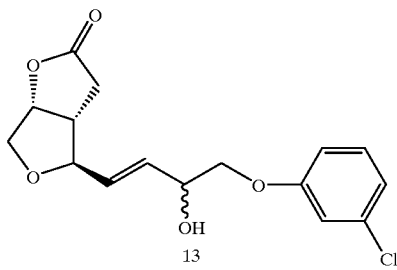

13

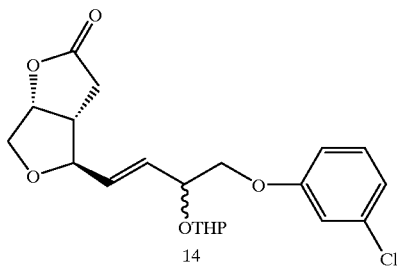

14

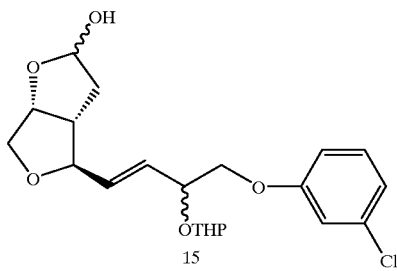

15

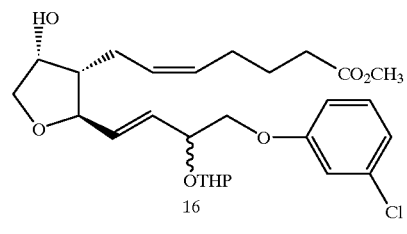

16

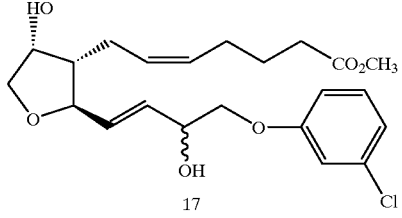

17

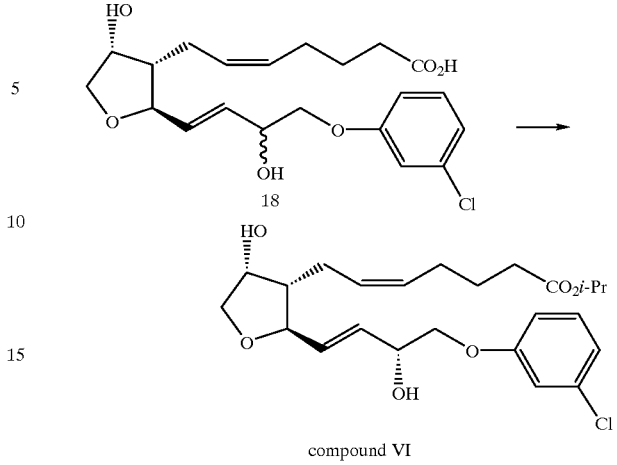

compound VI

A:[3aR, 4R(1E), 6aR]-4-[4-(3-Chlorophenoxy)-3-Oxo-1-Butenyl]Hexahydrofuro[3,4-b]-Furan-2-One (12):

A solution of dimethyl-3-(3-chlorophenoxy)-2-oxopropylphosphonate (2.34 g, 8 mmol) and LiCl (0.29 g, 6.9 mmol) in 15 mL of anhydrous THF was cooled to 0° C. under $N_2$ atmosphere and to it triethylamine (0.97 mL, 6.9 mmol) was added dropwise. A white slurry formed, which was stirred for 3 min at 0° C., at which time a solution of the aldehyde 11 (0.9 g, 5.76 mmol) in 15 mL of anhydrous THF was added to it. The resulting mixture was stirred at 0° C. for 1 h, and then partitioned between 100 mL of water and 250 mL of EtOAc. The layers were separated and the organic phase was washed with water and brine, and dried ($MgSO_4$). Filtration and solvent removal afforded a yellow liquid which was purified by chromatography on silica gel to yield 1.13 g of the enone 12 (60% yield) as a colorless, viscous liquid: $R_f$ 0.29 (60% EtOAc/hexane); $^1$H-NMR ($CDCl_3$) δ 7.22 (m, 1H), 6.85–7.08 (m, 3H), 6.79 (m, 1H), 6.65 (dd, 1H, J=16.2, 1.6 Hz), 5.10 (m, 1H), 4.69 (s, 2H), 4.38 (m, 1H), 4.10 (m, 2H), 2.88 (m, 2H), 2.57 (m, 1H).

B:[3aR, 4R(1E,3RS), 6aR]-4-[4-(3-Chlorophenoxy)-3-Hydroxy-1-Butenyl]Hexahydrofuro[3,4-b]Furan-2-One (13):

A mixture of 12 (1.0 g, 3.10 mmol) and $CeCl_3.7H_2O$ (2.3 g, 6.2 mmol) was taken up in a mixture of $CH_3OH$ (25 mL) and $CHCl_3$ (10 mL), and the solution was cooled to 0° C. To this cold solution $NaBH_4$ (0.23 g, 6.2 mmol) was added in small portions over a period of 5 min. (CAUTION: vigorous hydrogen gas evolution occurs). The resulting mixture was stirred for an additional 3 min at 0° C., and then poured into 100 mL of 0.5 N HCl solution. The aqueous solution was extracted with 3×50 mL of $CHCl_3$. The organic extracts were combined and washed with 3×50 mL of water and brine, and dried over anhydrous $MgSO_4$. Filtration and solvent removal afforded an oil which was purified by silica gel chromatography to give 0.71 g (70% yield) of 13 (a diastereomeric mixture of alcohols) as a colorless liquid: $R_f$ 0.14 (60% EtOAc/hexanes); $^1$H-NMR ($CDCl_3$) δ 7.21 (m, 1H), 6.95 (m, 2H), 6.78 (m, 1H), 5.89 (s, broad, 2H), 5.11 (m, 1H), 4.56 (m, 1H), 4.20 (m, 2H), 4.01 (m, 2H), 3.89 (m, 1H), 2.85 (m, 2H), 2.57 (m, 2H); $^{13}$C-NMR ($CDCl_3$) δ 175.62 (C=O), 158.96 (O—Ar), 134.93 (Cl—Ar), 130.95 and 130.80 (CH), 130.33 (CH), 129.86 and 129.75 (CH), 121.55 (CH), 115.02 (CH), 113.00 (CH), 84.57 and 84.51

(CH), 84.07 (CH), 72.48 (CH$_2$), 71.68 (CH$_2$), 69.82 and 69.76 (CH), 44.80 (CH), 32.49 (CH$_2$).

C:[3aR, 4R(1E,3RS), 6aR]-4-[4-(3-Chlorophenoxy)-3-(Tetrahydropyran-2-yl)Oxy-1-Butenyl]-Hexahydrofuro[3,4-b]Furan-2-One (14):

A solution of 13 (0.71 g, 2.19 mmol) in 20 mL of CH$_2$Cl$_2$ was cooled to 0° C. To this 0.5 mL (4.38 mmol) of 3,4-dihydro-2H-pyran was added followed by a catalytic amount of p-toluenesulfonic acid (10 mg). The reaction was stirred at 0° C. for 15 min and then quenched by the addition of 10 mL of a saturated aqueous solution of NaHCO$_3$. The layers were separated and the aqueous layer was extracted with 2×10 mL of dichloromethane. The combined organic extracts were dried (MgSO$_4$), filtered and concentrated. The product 14 (0.78 g, 91% yield) was isolated as a colorless liquid after chromatography of the crude on silica gel: R$_f$0.28 (60% EtOAc/hexane).

D:Methyl [2R(1E,3RS), 3S(5Z), 4R]-7-[Tetrahydro-2-[4-(3-Chlorophenoxy)-3-(Tetrahydropyran-2-yl)Oxy-1-Butenyl]-4-Hydroxy-3-Furanyl]-5-Heptenoate (16):

A solution of the lactone 14 (0.78 g, 1.9 mmol) in 20 mL of anhydrous THF was cooled to −78° C. under a N$_2$ atmosphere, and diisobutylaluminum hydride (DIBAL-H, 1.9 mL, 1.5 M in toluene, 2.8 mmol) was added to it dropwise. The resulting mixture was stirred at −78° C. for 1.5 h and then quenched at the same temperature by the careful addition of 5 mL of methanol. The mixture was allowed to warm to room temperature, diluted with 50 mL of EtOAc and treated with 100 mL of a saturated, aqueous potassium sodium tartrate solution, with vigorous stirring, for 1 h. The layers were separated and the aqueous layer was extracted with 3×10 mL of EtOAc. The combined organic extracts were dried (MgSO$_4$), filtered and concentrated. The crude product thus obtained was purified by passage through a short pad of silica gel to afford the intermediate lactol 15 (0.68 g, 87% yield) as a colorless liquid: R$_f$0.15 (60% EtOAc/hexane).

To a suspension of (4-carboxybutyl)triphenylphosphonium bromide (2.2 g, 4.9 mmol) in 20 mL anhydrous THF at 0° C., potassium tert-butoxide (t-BuOK, 10.0 mL, 1.0 M THF, 10.0 mmol) was added dropwise and the mixture was stirred at 0° C. for 30 min. A solution of the lactol 15 obtained above (0.68 g, 1.65 mmol) in 50 mL of THF was then added to it dropwise. The resulting mixture was allowed to warm to room temperature and was stirred at that temperature for 16 h. The reaction was quenched by pouring it into a saturated aqueous solution of ammonium chloride (50 mL) which had been acidified to pH 2–3 with dilute aqueous HCl solution. The mixture was extracted with EtOAc (5×25 mL), and the combined organic extracts were washed with water (1×25 mL) and brine (1×25 mL) and dried over anhydrous Na$_2$SO$_4$. The solution was filtered, concentrated to approximately 10 mL and then cooled to 0° C. This solution was treated with an excess of ethereal diazomethane at 0° C. The excess diazomethane was evaporated off by bubbling N$_2$ through the solution for 1 h. The resulting pale yellow solution was concentrated and applied to a column of silica gel for purification by chromatography. The methyl ester 16 (0.38 g, 50% yield, mixture of diastereomers) was isolated as a colorless liquid: R$_f$0.27 (60% EtOAc/hexane).

E:Methyl [2R(1E,3RS), 3S(5Z), 4R]-7-[Tetrahydro-2-[4-(3-Chlorophenoxy)-3-Hydroxy-1-Butenyl]-4-Hydroxy-3-Furanyl]-5-Heptenoate (17):

The compound 16 (0.37 g, 0.74 mmol) was dissolved in a mixture of 10 mL of methanol and 0.5 mL of water. The solution was cooled to 0° C. and to it was added about 10 drops of 12 N HCl. The resulting mixture was stirred at 0° C. for 15 min and then at room temperature for 45 min, at which time the reaction was quenched with solid NaHCO$_3$ (0.2 g). The mixture was transferred to a separatory funnel containing 25 mL each of CHCl$_3$ and saturated aqueous solution of NaHCO$_3$. The layers were separated and the aqueous layer was extracted with 4×25 mL of CHCl$_3$. The combined organic extracts were dried (Na$_2$SO$_4$), filtered and concentrated. The crude was purified by chromatography on silica gel to afford the diol 17 (0.28 g, 88% yield, mixture of diastereomers) as a colorless liquid: R$_f$0.18 (80% EtOAc/hexane); $^1$H-NMR (CDCl$_3$) δ 7.20 (m, 2H), 6.80–6.92 (m, 3H), 5.87 (m, 2H), 5.45 (m, 2H), 4.58 (m, 1H), 4.35 (m, 1H), 3.80–4.20 (m, 6H), 3.66 (s, 3H), 2.22–2.60 (m, 4H), 2.15 (m, 4H), 1.69 (m, 2H); MS m/z at 447 for (M+Na)$^+$.

F:Isopropyl [2R(1E,3R), 3S(5Z), 4R]-7-[Tetrahydro-2-[4-(3-Chlorophenoxy)-3-Hydroxy-1-Butenyl]-4-Hydroxy-3-Furanyl]-5-Heptenoate (VI):

The diastereomeric mixture of methyl esters 17 (0.28 g, 0.65 mmol) was dissolved in 20 mL of methanol containing 2 mL of water. To this solution 0.2 g (4.76 mmol) of LiOH was added and the resulting mixture was stirred at room temperature for 5.5 h. The reaction mixture was then transferred to a separatory funnel containing 50 mL of CHCl$_3$ and 25 mL of a 1N aqueous HCl solution; the layers were separated and the aqueous phase was extracted with 4×25 mL portions of CHCl$_3$. The organic extracts were combined and washed with 3×10 mL of water and 1×25 mL of brine and dried over anhydrous Na$_2$SO$_4$. The solution was filtered, concentrated and purified by HPLC (RP-18, acetonitrile/water/TFA) to afford 18 (0.25 g, 93% yield, diastereomeric mixture) as a clear colorless liquid: $^1$H-NMR (CDCl$_3$) δ 7.22 (m, 2H), 6.85–7.05 (m, 3H), 5.86 (m, 2H), 5.44 (m, 2H), 4.84 (broad, 2H), 4.61 (m, 1H), 4.37 (m, 1H), 3.86–4.20 (m, broad, 6H), 2.00–2.65 (m, 6H), 1.50–1.95 (m, 3H); $^{13}$C-NMR (CDCl$_3$) δ 177.58 (C=O), 159.08 (O—Ar), 134.89 (Cl—Ar), 133.22 (CH), 132.46 (CH), 130.28, 129.84 (CH), 128.01 (CH), 121.43 (CH), 115.13, 115.10 (CH), 113.02 (CH), 82.26, 82.03 (CH), 75.54, 75.48 (CH$_2$), 72.58, 72.50 (CH), 71.59, 71.55 (CH$_2$), 70.48, 70.03 (CH), 51.39, 51.34 (CH), 32.68 (CH$_2$), 26.19 (CH$_2$), 24.41, 24.30 (CH$_2$), 22.33, 22.18 (CH$_2$); MS m/z at 433 for (M+Na)$^+$.

A solution of the acid 18 (0.25 g, 0.61 mmol) in 15 mL of acetone was treated with 1,8-diazabicyclo[5.4.0]undec-7-ene (DBU; 0.66 mL, 4.4 mmol) for 30 min at room temperature. Isopropyl iodide (0.36 mL, 3.7 mmol) was then added to the reaction mixture, and the resulting solution was stirred at room temperature for 18 h. The solvent was then evaporated and the residue was partitioned between 50 mL of Et$_2$O and 10 mL of water. The layers were separated and the organic layer was washed with 3×10 mL of a 10% aqueous CuSO$_4$ solution and 1×10 mL of brine. The organic phase was dried (Na$_2$SO$_4$), filtered and concentrated. The crude was applied to a column of silica gel and the two diastereomeric esters were isolated separately, yielding compound VI (81 mg, 32% yield) as a colorless oil: R$_f$ 0.54 (EtOAc); $^1$H-NMR (CDCl$_3$) δ 7.19 (m, 1H), 6.92 (m, 2H), 6.80 (m, 1H), 5.86 (m, 2H), 5.42 (m, 2H), 5.05 (septet, J=6.2 Hz, 1H), 4.58 (m, 1H), 4,35 (m, 1H), 4.20–3.82 (broad m, 5H), 2.68 (d, J=4.5 Hz, 1H), 2.45–2.00 (m, 7H), 1.89–1.60 (m, 4H), 1.24 (d, J=6.5 Hz, 6H); $^{13}$C-NMR (CDCl$_3$) δ 173.42, 159.20, 134.89, 132.48, 130.57, 130.35, 130.25, 128.06, 121.35, 115.11, 113.05, 82.02, 75.43, 72.70, 71.87, 70.14, 67.71, 51.09, 33.99, 26.63, 24.77, 22.57, 21.81; MS m/z at 475 for (M+Na).

EXAMPLE 3

Synthesis of Isopropyl [2R(1E,3S),3R(5Z),4S]-7-[Tetrahydro-4-Chloro-2-(3-Cyclohexyl-3-Hydroxy-1-Propenyl)-3-Furanyl]-3-Oxa-5-Heptenoate (VII)

Compound VII may be prepared as described by the following Scheme 3.

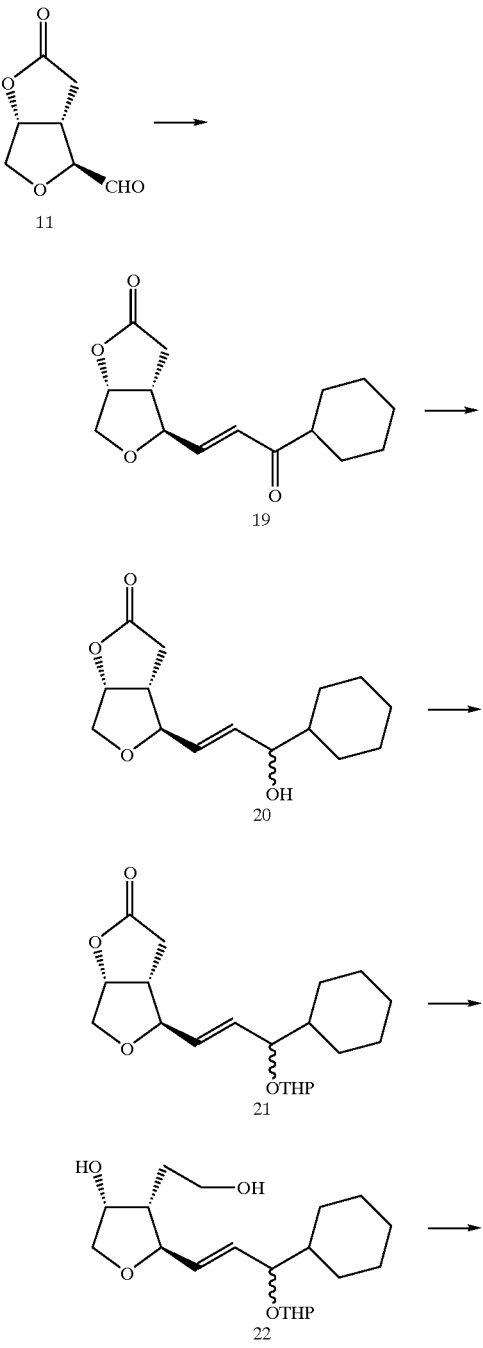

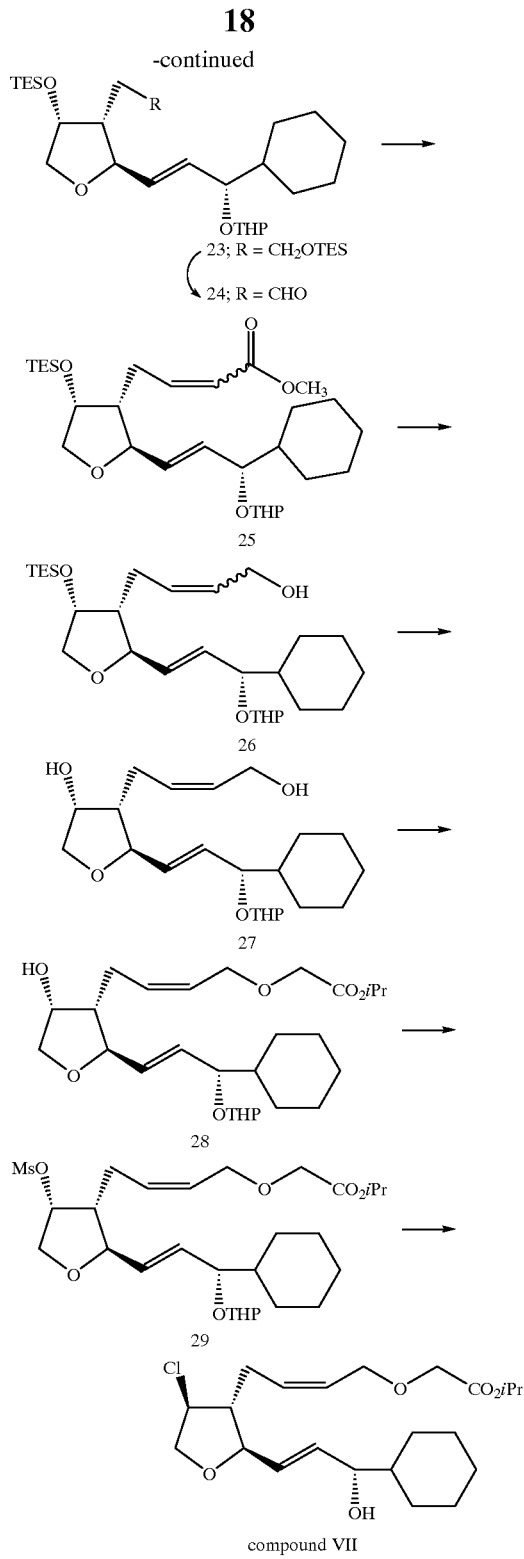

A: [3aR, 4R(1E), 6aR]-4-(3-Cyclohexyl-3-Oxopropenyl) Hexahydrofuro[3,4-b]Furan-2-One (19):

A 500 mL 1-neck flask was charged with dimethyl-(2-cyclohexyl-2-oxo)ethylphosphonate (6.9 g, 29.6 mmol), LiCl (1.07 g, 25.4 mmol) and 40 mL of anhydrous THF. The mixture was cooled to 0° C. and triethylamine (3.6 mL, 25.4 mmol) was added to it in a dropwise manner. The white slurry formed was stirred for 10 min and then a solution of (3aR,4S,6aR)-hexahydro-2-oxofuro[3,4-b]furan-4- carboxaldehyde (11; 3.31 g, 21.2 mmol) in a mixture of 60 mL of anhydrous THF and 10 mL of anhydrous $CH_2Cl_2$ was added to it dropwise. The resulting mixture was allowed to warm to room temperature and was stirred at that temperature for 18 h. The reaction mixture was worked up (250 mL of EtOAc and 50 mL of water) and purified by silica gel chromatography. The white solid obtained was recrystallized from hexane using a minimum amount of EtOAc to effect solubilization. The enone 19 (2.2 g, 43% yield) was isolated as white needles: mp. 80.0–82.5° C.; $R_f$0.37 (60% EtOAc/hexane); $[\alpha]_D^{22}$+47.9°(c=0.6, $CH_3OH$); $^1$H-NMR ($CDCl_3$) δ 6.72 (dd, J=16.6, 4.5 Hz, 1H), 6.45 (dd, J=16.6, 1.5 Hz, 1H), 5.12 (m, 1H), 4.38 (m, 1H), 4.20–4.05 (m, 2H), 2.85 (m, 2H), 2.52 (m, 2H), 1.95–1.58 (m, 5H), 1.50–1.10 (m, 5H); $^{13}$C-NMR($CDCl_3$) δ 202.32, 175.18, 141.00, 127.81, 83.86, 83.80, 72.74, 49.64, 44.65, 32.86, 28.31, 25.76, 25.57; MS m/z at 265 for $(M+H)^+$.

B:[3aR, 4R(1E,3RS), 6aR]-4-(3-Cyclohexyl-3-Hydroxypropenyl)Hexahydrofuro[3,4-b]Furan-2-One (20):

To a solution of $CeCl_3.7H_2O$ (2.23 g, 6.0 mmol) in 50 mL of methanol, the enone 19 (0.8 g, 3.0 mmol) was added and the resulting solution was cooled to 0° C. The cold solution was treated with solid $NaBH_4$ in small portions (0.23 g, 6.0 mmol) over a period of 5 min. (CAUTION: vigorous $H_2$ gas evolution occurs). After an additional 3 min at 0° C., the reaction was quenched by pouring it into 50 mL of a 0.5 N aqueous HCl solution. The aqueous layer was extracted with 4×75 mL of $CHCl_3$ and the organic extracts were washed with water and brine and dried ($MgSO_4$). Filtration and solvent removal afforded the crude, which was purified by silica column chromatography to afford 20 (0.69 g, 85% yield) as an equimolar mixture of two diastereomers: $R_f$0.2 (60% EtOAc/hexane); $^1$H-NMR ($CDCl_3$) δ 5.77 (m, 2H), 5.12 (m, 1H), 4.25–3.82 (m, 4H), 2.78 (m, 2H), 2.45 (m, 1H), 1.90–0.85 (broad m, 12H).

C:[3aR, 4R(1E,3RS), 6aR]-4-[3-Cyclohexyl-3-(Tetrahydropyran-2-yl)Oxypropenyl]Hexahydrofuro[3,4-b]Furan-2-One (21):

A solution of the alcohol 20 (0.69 g, 2.6 mmol) and 3,4-dihydro-2H-pyran (0.6 mL, 5.2 mmol) in 25 mL of $CH_2Cl_2$ was cooled to 0° C. After 3 min, a catalytic amount of p-toluenesulfonic acid (20 mg) was added. The reaction mixture was stirred at 0° C. for 20 min and then quenched by the addition of 10 mL of a saturated aqueous solution of $NaHCO_3$. The layers were separated and the organic phase was washed with brine and dried ($K_2CO_3$). The compound 21 (0.8 g, 88% yield) was isolated as a colorless liquid after chromatography of the crude on silica: $R_f$0.5 (60% EtOAc/hexane).

D:[2R(1E,3S),3R, 4R]-2-[3-Cyclohexyl-3-(Tetrahydropyran-2-yl)Oxy-1-Propenyl]-3-(2-Triethylsilyloxyethyl)-4-Triethylsilyloxytetrahydrofuran (23):

A suspension of lithium aluminum hydride (2.0 g, 54 mmol) in dry THF (100 mL) was cooled to 0° C., and to it a solution of the lactone 21 (9.42 g, 27 mmol) in THF (100 mL) was added dropwise. The mixture was gradually allowed to warm to room temperature, and was stirred at that temperature for 14 h. The reaction was then cooled to 0° C. in an ice bath, and quenched by adding 10 mL of methanol dropwise. The ice bath was removed and the suspension was sequentially treated with 2 mL of water, 2 mL of a 15% aqueous NaOH solution and 6 mL of water. The resulting suspension was filtered through a pad of $MgSO_4$, and the filter cake was washed with 100 mL of EtOAc. The filtrate was concentrated and the residue was subjected to silica gel chromatography to afford 7.14 g (75% yield) of the diol 22 (mixture of diastereomers) as a colorless liquid: $R_f$0.25 (EtOAc); $^1$H-NMR ($d_6$-DMSO) δ (partial spectrum) 5.65–5.30 (m, broad, 2H, olefinic), 4.75 (m, 1H, O$\underline{H}$), 4.45 (m, 1H, O$\underline{H}$).

A solution of the diol 22 (1.84 g, 5.2 mmol) in $CH_2Cl_2$ (60 mL) was cooled to 0° C., and to it was added triethylamine (4.4 mL, 31.2 mmol) and a catalytic amount of N,N-dimethylamino pyridine (DMAP, 50 mg). The resulting mixture was stirred for 3 min, and then triethylsilyl chloride (2.6 mL, 15.6 mmol) was added to it. The reaction mixture was stirred for 1 h at 0° C., and then at room temperature for an additional hour. The reaction was then poured into 100 mL of water, and the biphasic mixture was extracted with ether (5×50 mL). The organic extracts were combined and washed with brine and dried over anhydrous $K_2CO_3$. Filtration and solvent removal gave an oil, which was subjected to column chromatography on silica gel; the two C15 diastereomers were separated and the desired isomer 23 (1.63 g, 54%) was obtained as a colorless oil: $R_f$0.21 (20% $Et_2O$/hexane); $^1$H-NMR ($CDCl_3$) δ 5.50 (m, 2H), 4.70 (broad m, 1H), 4.32 (broad m, 1H), 4.15–3.40 (broad, 8H), 2.15–1.45 (broad, 15H), 1.35–0.80 (m, 20H), 0.60 (m, 12H).

E:[2R(1E,3S),3R,4R]-2-[Tetrahydro-2-[3-Cyclohexyl-3-(Tetrahydropyran-2-yl)Oxy-1-Propenyl]-4-Triethylsilyloxy-3-Furanyl]Acetaldehyde (24):

A solution of oxalyl chloride (2.8 mL, 2.0 M/$CH_2Cl_2$, 5.60 mmol) in 15 mL of $CH_2Cl_2$ was cooled to –78° C., and to it a solution of DMSO (0.80 mL, 11.20 mmol) in 1.0 mL of $CH_2Cl_2$ was added dropwise. The mixture was stirred for 3 min, at which time a solution of the substrate 23 (1.63 g, 2.80 mmol) in 15 mL of $CH_2Cl_2$ was added to it. The resulting mixture was stirred at –78° C. for 3 h, and then treated with triethylamine (2.0 mL, 14.0 mmol). The cold temperature bath was removed and the reaction was allowed to warm to room temperature and then worked up by partitioning between water and $CH_2Cl_2$. The crude was subjected to silica gel chromatography to afford 24 (1.02 g, 78% yield) as a colorless liquid: $R_f$0.15 (10% EtOAc/hexane); $^1$H-NMR ($CDCl_3$) δ (partial spectrum) 9.84 (s, 1H, aldehyde), 5.53 (m, 2H, olefinic), 4.69 (m, 1H), 4.50 (m, 1H), 4.15 (m, 2H), 2.80 (m, 1H).

F:Methyl [2R(1E,3S),3R(2EZ),4R]-4-[Tetrahydro-2-[3-Cyclohexyl-3-(Tetrahydropyran-2-yl)Oxy-1-Propenyl]-4-Triethylsilyloxy-3-Furanyl]-2-Butenoate (25):

A solution containing bis(2,2,2-trifluoroethyl) (methoxycarbonylmethyl)phosphonate (0.86 g, 2.6 mmol) and 18-crown-6 (1.74 g, 6.6 mmol) in THF (30 mL) was cooled to –78° C., and to it a solution of potassium bis (trimethylsilyl)amide (KHMDS, 5.2 mL, 0.5 M in toluene, 2.6 mmol) was added dropwise. The resulting solution was stirred at –78° C. for 20 min, at which time a solution of the aldehyde 24 (1.02 g, 2.2 mmol) in 10 mL of THF was introduced via cannula. The reaction was stirred at the same temperature for 2 h, after which it was rapidly warmed to 0° C. (ice bath) and quenched at that temperature by adding 50 mL of a saturated aqueous solution of $NH_4Cl$. The resulting mixture was allowed to warm to room temperature and was partitioned between water and EtOAc. The organic layers were combined, washed with water, brine and dried (MgSO4). The product 25 (0.94 g, 81% yield), as a mixture of diastereomers, was isolated as a colorless liquid after chromatography on silica: $R_f$0.50 (30% EtOAc/hexane); $^1$H-NMR ($CDCl_3$) δ (major isomer only) 6.28 (m, 1H), 5.80 (m, 1H), 5.55 (m, 2H), 4.68 (m, 1H), 4.38 (m, 1H), 4.18 (m, 1H), 4.02 (m, 1H), 3.70 (s, 3H), 2.80 (m, 2H), 0.95 (m, 9H), 0.61 (m, 6H).

G:[2R(1E,3S)3S(2Z),4R]-4-[Tetrahydro-2-[3-Cyclohexyl-3-(Tetrahydropyran-2-yl)Oxy-1-Propenyl]-4-Hydroxy-3-Furanyl]-2-Butenol (27):

A solution of the enoate 25 (0.94 g, 1.8 mmol) in 20 mL of THF was cooled to 0° C., and DIBAL-H (3.6 mL, 1.5 M in toluene, 5.4 mmol) was added to it dropwise over 5 min. The reaction mixture was stirred at 0° C. for 2 h, and then quenched at the same temperature by carefully adding 5 mL of methanol. The reaction was worked up by stirring it with a saturated aqueous solution of potassium sodium tartrate for 1 h at room temperature. The layers were separated and the aqueous layer was extracted with 3×25 mL of ether. The organic extracts were combined and dried, filtered and evaporated to afford an oil which was purified by passage through a short plug of silica. The mixture of allylic alcohol isomers 26 (0.77 g, 82% yield) was obtained as a colorless liquid: $R_f$ 0.23 (30% EtOAc/hexane).

A solution of the allylic alcohol mixture obtained above (0.77 g, 1.56 mmol) in 50 mL of THF was treated with tetra-n-butylammonium fluoride (8.0 mL, 1.0 M in THF, 8.0 mmol) at room temperature for 10 min. The mixture was then poured into water and extracted with ether (3×25 mL). The combined ether layers were washed with water and brine and dried ($MgSO_4$); the crude oil was subjected to chromatography to afford the desired major isomer 27 (0.54 g, 91% yield) as a white semi-solid: $R_f$ 0.31 (EtOAc); $^1$H-NMR (CDCl$_3$) δ (partial spectrum) 5.90–5.45 (broad m, 4H), 4.68 (m, 1H), 4.35 (m, 2H), 4.20–3.65 (broad m, 6H), 3.45 (m, 1H), 2.60 (m, 2H); MS m/z at 403 for (M+Na)$^+$.

H:Isopropyl [2R(1E,3S),3S(5Z),4R]-7-[Tetrahydro-2-[3-Cyclohexyl-3-(Tetrahydropyran-2-yl)Oxy-1-Propenyl]-4-Hydroxy-3-Furanyl]-3-Oxa-5-Heptenoate(28):

A solution of the diol 27 (0.54 g, 1.42 mmol) in 15 mL of toluene was cooled to 0° C., and to it were added nBu$_4$NHSO$_4$ (0.1 g) and aqueous NaOH (15 mL, 25% w/v). The resulting mixture was stirred vigorously for 5 min, at which time isopropyl bromoacetate (0.77 g, 4.26 mmol) was added to it dropwise. After stirring at 0° C. for an additional 30 min, the reaction mixture was poured into ether/water mixture (50 mL each). The layers were separated and the aqueous layer was extracted with ether (3×25 mL). The organic extracts were combined and washed with a saturated aqueous solution of KH$_2$PO$_4$ (10 mL), water (10 mL) and brine (10 mL) and dried (MgSO$_4$). The crude oil was subjected to silica column chromatography to afford 28 (0.45 g, 66% yield) as a colorless liquid: $R_f$ 0.28 (60% EtOAc/hexane); $^1$H-NMR (CDCl$_3$) δ 5.72 (m, 2H), 5.52 (m, 2H), 5.13 (septet, J=6.7 Hz, 1H), 4.70 (m, 1H), 4.45–4.25 (m, 2H), 4.20–3.68 (broad m, 8H), 3.45 (m, 1H), 3.28 (m, 1H), 2.60 (m, 1H), 2.08–1.35 (broad m, 15H), 1.28 (d, J=7.2 Hz, 6H), 1.25–0.90 (broad m, 3H).

I:Isopropyl [2R(1E,3S),3R(5Z),4S]-7-[Tetrahydro-4-Chloro-2-8 3-Cyclohexyl-3-Hydroxy-1-Propenyl]-3-Furanyl]-3-Oxa-5-Heptenoate (Compound VII):

A solution of the ester 28 (0.2 g, 0.4 mmol) in 5.0 mL of anhydrous pyridine was cooled to 0° C., and to it methanesulfonyl chloride (80 mL, 1.04 mmol) was added. The resulting solution was stirred at 0° C. for 5 min and then at room temperature for 24 h. The reaction mixture was poured into 50 mL of ether and washed with 4×25 mL of a saturated aqueous CuSO$_4$ solution and dried (MgSO$_4$). The crude was purified by passage through a column of silica to afford 0.21 g (97% yield) of the mesylate 29 as a pale yellow liquid: $R_f$ 0.30 (60% EtOAc/hexane).

The mesylate 29 obtained above (0.21 g, 0.39 mmol), and LiCl (0.17 g, 4.0 mmol) were dissolved in 10 mL of anhydrous DMF and the resulting solution was heated at 65–75° C. for 24 h. The reaction was cooled to room temperature, and poured into ether/water. The layers were separated, the aqueous layer was extracted with 3×25 mL of ether; the organic layers were combined and washed with 2×10 mL water and brine and dried (Na$_2$SO$_4$). Filtration and solvent removal followed by chromatography of the crude on silica afforded compound VII (51 mg, 32% yield) as a colorless oil: $R_f$ 0.50 (60% EtOAc/hexane); $^1$H-NMR (CDCl$_3$) δ 5.82–5.60 (broad m, 4H), 5.08 (septet, J=6.7 Hz, 1H), 4.20–3.82 (broad m, 10H), 2.32 (m, 2H), 2.15 (m, 1H), 1.90–1.55 (broad m, 8H), 1.50–0.90 (broad m, 8H), 1.28 (d,J=7.3 Hz, 6H); $^{13}$C-NMR(CDCl$_3$) δ 169.92, 135.26, 130.32, 130.19, 127.86, 83.97, 76.57, 74.22, 68.63, 67.69, 66.60, 59.96, 54.73, 43.61, 28.90, 28.48, 27.87, 26.54, 26.16, 26.09, 21.89; MS m/z at 437 for (M+Na)$^+$.

EXAMPLE 4

Synthesis of Isopropyl [2R(1E,3R),3S(4Z),4R]-7-[Tetrahydro-2-[4-(3-Chlorophenoxy)-3-Hydroxy-1-Butenyl]-4-Hydroxy-3-Furanyl]-4-Heptenoate (VIII)

Compound VIII may be prepared as described in the following Scheme 4.

Scheme 4:
Synthesis of compound VIII

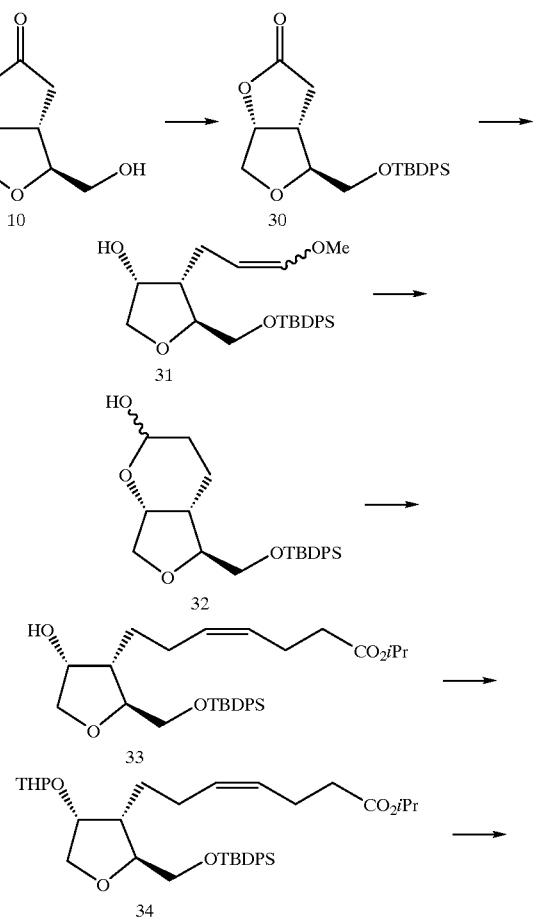

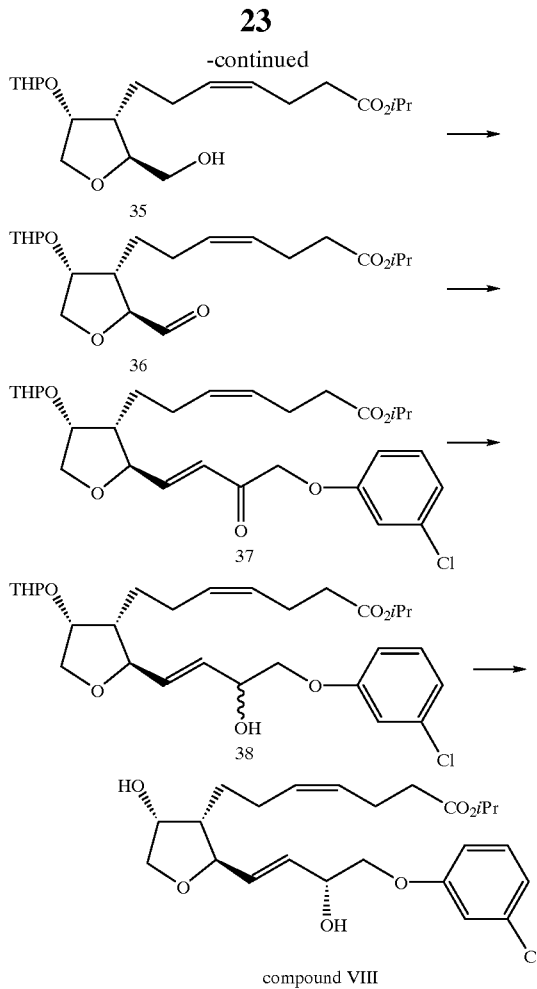

compound VIII

A: (3aR,4S,6aR)-4-(tert-Butyldiphenylsilyloxy) Methylhexahydrofuro[3,4-b]Furan-2-One (30):

A mixture of alcohol 10 (5.0 g, 31.6 mmol) and imidazole (4.3 g, 63.2 mmol) was dissolved in 100 mL of anhydrous DMF. To this solution tert-butyldiphenylsilyl chloride (10.4 g, 38.0 mmol) was added and the resulting mixture was stirred at room temperature for 14 h. The solvent was evaporated and the residue was taken up in 100 mL of EtOAc, washed with water (2×50 mL), dilute aqueous solution of HCl (2×50 mL) and brine and dried (MgSO4). The solvent was evaporated and the crude was purified by chromatography on silica gel to afford 30 (12.4 g, quantitative yield) as a white solid: $R_f$ 0.6 (60% EtOAc/hexanes); $^1$H-NMR (CDCl$_3$) δ 7.65 (m, 4H), 7.42 (m, 6H), 5.10 (m, 1H), 4.25 (dd, J=12, 4 Hz, 1H), 4.05 (dd, J=12, 2 Hz, 1H), 3.85 (m, 1H), 3.75 (m, 2H), 3.00 (m, 1H), 2.82 (dd, J=16, 7 Hz, 1H), 2.45 (dd, J=16, 2 Hz, 1H), 1.05 (s, 9H).

B: Isopropyl [2S,3S(4Z),4R]-7-[Tetrahydro-2-(tert-Butyldiphenylsilyloxy)Methyl-4-Hydroxy-3-Furanyl]-4-Heptenoate (33):

A solution of the lactone 30 (5.7 g, 14.5 mmol) in 150 mL of anhydrous THF was cooled to −78° C. under an inert atmosphere, and to it DIBAL-H (14.5 mL, 1.5 M in toluene, 21.7 mmol) was added dropwise. The resulting mixture was stirred at −78° C. for 1.5 h and was then quenched at the same temperature by the addition of 5 mL of methanol. The reaction was warmed to room temperature, an equal volume of a saturated aqueous solution of potassium sodium tartrate was added to it and the resulting slurry was stirred at room temperature for 1 h. The layers were separated, and the aqueous layer was extracted with 3×25 mL of EtOAc. The organic layers were combined and washed with brine and dried (MgSO$_4$). The solution was filtered and concentrated and the crude was purified by passage through a short column of silica gel to afford the intermediate lactol (5.6 g, quantitative yield) as a colorless oil: $R_f$ 0.5 (60% EtOAc/hexanes).

A suspension of (methoxymethyl)triphenylphosphonium chloride (2.5 g, 7.5 mmol) in 70 mL of dry THF was cooled to 0° C. under a N$_2$ atmosphere. To this solution potassium tert-butoxide (t-BuOK, 9.0 mL, 1.0 M in THF, 9.0 mmol) was added dropwise and stirring was continued at 0° C. for an additional 20 min. At this time a solution of the lactol obtained above (1.0 g, 2.5 mmol) in 30 mL of dry THF was added to it, and the resulting mixture was stirred at 0° C. for 1.5 h. The reaction was then worked up by pouring it into 50 mL of a saturated aqueous solution of KH$_2$PO$_4$, the layers were separated and aqueous layer was extracted with 3×25 mL of EtOAc. The combined organic layers were washed with water and brine and dried (MgSO$_4$); solvent removal and chromatography of the crude on silica afforded the enolether 31 (0.89 g, 83% yield) as a colorless liquid: $R_f$ 0.6 (60% EtOAc/hexanes).

A solution containing enolether 31 (2.45 g, 5.7 mmol), p-toluenesulfonic acid (0.1 g) and water (10 mL) in 150 mL of THF was heated at reflux for 3 h. The mixture was then cooled to room temperature and poured into 50 mL of a saturated aqueous solution of NaHCO$_3$. The layers were separated and aqueous layer was extracted with EtOAc. The organic extracts were combined and dried (MgSO$_4$) and the crude product was subjected to chromatography on silica to afford 32 (1.44 g, 60% yield) as a colorless liquid. This material was used in the next reaction: $R_f$ 0.28 (50% EtOAc/hexanes).

A suspension of (3-carboxypropyl)triphenylphosphonium bromide (4.5 g, 10.5 mmol) in 70 mL of dry THF was cooled to 0° C. and to it t-BuOK (21.0 mL, 1.0 M in THF, 21.0 mmol) was added dropwise. The resulting solution of the ylid was stirred for 30 min at 0° C. and to it a solution of the lactol 32 (1.44 g, 3.5 mmol) in 30 mL of dry THF was added dropwise over a period of 10 min. The reaction was allowed to warm to room temperature gradually, and was stirred at that temperature for 14 h. The mixture was then poured into 50 mL of a saturated aqueous solution of KH$_2$PO$_4$, and extracted with 3×25 mL of EtOAc. The organic extracts were combined and washed with brine and dried (MgSO$_4$). Filtration and solvent removal afforded an oily residue which was used immediately in the subsequent step.

The crude product from above was dissolved in 40 mL of acetone and the solution was treated with DBU (12.0 mL, 84 mmol) at room temperature for 10 min. Isopropyl iodide (7.0 mL, 70 mmol) was then introduced and the resulting mixture was stirred at room temperature for 18 h. Solvent was then evaporated and the residue was dissolved in 50 mL of EtOAc. This solution was washed sequentially with 3×25 mL of a saturated aqueous solution of KH$_2$PO$_4$, 1×10 mL of water and brine and dried over anhydrous MgSO$_4$. Filtration, solvent removal and chromatography of the crude on silica gel afforded the desired isopropyl ester 33 (1.18 g, 65% yield from 32) as a slightly yellow liquid: $R_f$ 0.2 (30% EtOAc/hexanes); $^1$H-NMR (CDCl$_3$) δ 7.71 (m, 4H), 7.40 (m, 6H), 5.38 (m, 2H), 5.00 (septet, J=6.4 Hz, 1H), 4.38 (m, 1H), 3.65–4.00 (broad m, 5H), 1.90–2.50 (broad m, 7H), 1.55 (m, 2H), 1.23 (d, J=7.2 Hz, 6H), 1.05 (s, 9H); MS m/z at 547 for (M+Na)$^+$.

C: Isopropyl [2S,3R(4Z),4R]-7-[Tetrahydro-2-Hydroxymethyl-4-(Tetrahydropyran-2-yl)Oxy-3-Furanyl]-4-Heptenoate (35):

A solution of the alcohol 33 (1.18 g, 2.3 mmol) and 3,4-dihydro-2H-pyran (0.3 mL, 3.4 mmol) in 50 mL of $CH_2Cl_2$ was cooled to 0° C. and to it a catalytic amount of p-toluenesulfonic acid (10 mg) was added. The resulting mixture was stirred at 0° C. for 25 min and was then quenched by the addition of 25 mL of a saturated aqueous solution of $NaHCO_3$. The mixture was warmed to room temperature, the layers were separated and the aqueous layer was extracted with 3×25 mL of $CH_2Cl_2$. The organic layers were combined and washed with brine and dried ($K_2CO_3$). The crude obtained after filtration and solvent removal was purified by passage through a short plug of silica to afford the intermediate tetrahydropyranyl ether 34 as colorless liquid: $R_f$ 0.4 (30% EtOAc/hexanes).

The silyl ether 34 thus obtained was dissolved in 20 mL of THF and the solution was treated with tetra-n-butylammonium fluoride (7.0 mL, 1.0 M in THF, 7.0 mmol) at room temperature for 2 h. The reaction mixture was then poured into water and was extracted with EtOAc (3×25 mL). The organic extracts were combined and dried ($MgSO_4$), filtered and concentrated. The crude was subjected to chromatography on silica to afford the alcohol 35 (0.72 g, 85% yield from 33) as a colorless liquid: $R_f$ 0.16 (50% EtOAc/hexanes); $^1$H-NMR ($d_6$-DMSO) δ (partial spectrum) 5.36 (m, 2H), 4.87 (septet, J=6.5 Hz, 1H), 4.60 (m, 2H), 1.18 (d, J=7.2 Hz, 6H).

D: Isopropyl [b 2S,3R(4Z),4R]-7-[Tetrahydro-2-Formyl-4-(Tetrahydropyran-2-yl)Oxy-3-Furanyl]-4-Heptenoate (36):

A solution of oxalyl chloride (2.0 mL, 2.0 M in $CH_2Cl_2$, 4.0 mmol) in 10 mL of dry $CH_2Cl_2$ was cooled to −78° C., and to it a solution of DMSO (0.56 mL, 8.0 mmol) in 5 mL of $CH_2Cl_2$ was introduced dropwise. After the mixture was stirred for 3 min at −78° C., a solution of the substrate 35 (0.72 g, 2.0 mmol) in 25 mL of $CH_2Cl_2$ was added to it dropwise. The mixture was stirred for 15 min, at which time triethylamine (1.7 mL, 12.0 mmol) was introduced, and stirring was continued for an additional 15 min. The reaction was gradually warmed to room temperature and then poured into 50 mL of water. The layers were separated and the water layer was extracted with 3×25 mL of $CH_2Cl_2$. The combined organic extracts were washed with water and brine and dried ($MgSO_4$). Filtration and solvent removal, followed by chromatography of the crude on silica afforded the aldehyde 36 (0.69 g, 94% yield) as a pale yellow liquid: $R_f$ 0.3 (50% EtOAc/hexanes); $^1$H-NMR ($CDCl_3$) δ (partial spectrum) 9.66 (d, J=3 Hz, 1H), 5.37 (m, 2H), 5.0 (septet, J=6.5 Hz, 1H), 1.24 (d, J=7.2 Hz, 6H).

E: Isopropyl [2R(1E),3R(4Z),4R]-7-[Tetrahydro-2-[4-(3-Chlorophenoxy)-3-Oxo-1-Butenyl]-4-(Tetrahydropyran-2-yl)Oxy-3-Furanyl]-4-Heptenoate (37):

A mixture of the aldehyde 36 (0.32 g, 0.87 mmol), dimethyl-3-(3-chlorophenoxy)-2-oxopropylphosphonate (1.0 g, 3.5 mmol) and LiCl (0.15 g, 3.5 mmol) was taken up in 40 mL of dry THF, and the solution was cooled to 0° C. under a $N_2$ atmosphere. To this solution, triethylamine (0.5 mL, 3.5 mmol) was added dropwise, and the resulting slurry was stirred at 0° C. for 1 h. The reaction was then quenched by pouring it into 50 mL of a saturated aqueous solution of $KH_2PO_4$. The organic layer was separated and the aqueous layer was extracted with 3×25 mL of EtOAc. The organic extracts were combined and washed with water and brine and dried ($MgSO_4$). The crude product mixture was subjected to chromatography on silica to afford the enone 37 (0.34 g, 73% yield) as a pale yellow liquid: $R_f$ 0.6 (60% EtOAc/hexanes); $^1$H-NMR ($CDCl_3$) δ (partial spectrum) 6.70–7.20 (broad m, 5H), 6.12 (d, J=16.7 Hz, 1H), 5.36 (m, 2H), 5.0 (septet, J=6.5 Hz, 1H), 4.73 (s, 2H), 1.23 (d, J=7.5 Hz, 6H).

F: Isopropyl [2R(1E,3RS),3R(4Z),4R]-7-[Tetrahydro-2-[4-(3-Chlorophenoxy)-3-Hydroxy-1-Butenyl]-4-(Tetrahydropyran-2-yl)Oxy-3-Furanyl]-4-Heptenoate (38):

A mixture of the enone 37 (0.34 g, 0.64 mmol) and $CeCl_3 \cdot 7H_2O$ (0.47 g, 1.27 mmol) was dissolved in 30 mL of methanol and the solution was cooled to −5° C. $NaBH_4$ (47 mg, 1.27 mmol) was added to the solution in small portions over a period of 3 min. The mixture was stirred for an additional 3 min and the reaction was quenched at −5° C. by the addition of 10 mL of a saturated aqueous solution of $NH_4Cl$. The resulting slurry was warmed to room temperature and partitioned between $CHCl_3$ and water. The aqueous layer was extracted with 3×25 mL of $CHCl_3$ and the combined organic extracts were washed with 2×10 mL of water and brine. The organic layer was dried, filtered and concentrated and the crude was purified by chromatography on silica to afford the reduction product 38 (0.30 g, 87% yield) as a colorless liquid: $R_f$ 0.24 (50% EtOAc/hexanes).

G: Isopropyl [2R(1E,3R),3S(4Z),4R]-7-[Tetrahydro-2-[4-(3-Chlorophenoxy)-3-Hydroxy-1-Butenyl]-4-Hydroxy-3-Furanyl]-4-Heptenoate (Compound VIII):

The allyl alcohol 38 (0.30 g, 0.55 mmol) was dissolved in a mixture of 10 mL of methanol and 1.0 mL of water, and the solution was cooled to 0° C. Approximately 10 drops of 12 N HCl was added to it dropwise and the mixture was stirred at 0° C. for 15 min and then at room temperature for 1 h. The reaction was then quenched by the addition of solid $NaHCO_3$, and the suspension was partitioned between $CHCl_3$/water. The layers were separated and the aqueous layer was extracted with 3×25 mL of $CHCl_3$. The organic extracts were combined and washed with water (2×10 mL) and brine and dried ($Na_2SO_4$). Filtration and solvent removal gave an oil which was subjected to silica gel chromatography. The two diastereomers were isolated separately, and the desired compound VIII (61 mg, 25% yield) was obtained as colorless liquid: $R_f$ 0.15 (60% EtOAc/hexanes); $^1$H-NMR ($CDCl_3$) δ 7.17 (m, 1H), 6.90 (m, 2H), 6.78 (m, 1H), 5.84 (m, 2H), 5.35 (m, 2H), 5.00 (septet, J=6.4 Hz, 1H), 4.55 (m, 1H), 4.40 (m, 1H), 3.80–4.15 (broad m, 5H), 1.90–2.65 (broad m, 8H), 1.75 (m, 2H), 1.45 (m, 2H), 1.21 (d, J=7.4 Hz, 6H); $^{13}$C-NMR ($CDCl_3$) δ 173.08, 159.19, 134.90, 132.69, 130.68, 130.57, 130.26, 128.07, 121.35, 115.09, 113.04, 82.21, 75.45, 72.62, 71.83, 70.12, 67.94, 50.84, 34.36, 25.78, 24.55, 22.70, 21.89, 21.80; HRMS m/z calculated for $C_{24}H_{33}O_6ClNa$ (M+Na$^+$) 475.185884, found 475.18588.

EXAMPLE 5

Synthesis of Isopropyl [2S(3S),3R(5Z),4S]-7-[Tetrahydro-4-Chloro-2-(3-Cyclohexyl-3-Hydroxy-1-Propynyl)-3-Furanyl]-3-Oxa-5-Heptenoate (IX)

Compound IX may be prepared as described in the following Scheme 5.

Scheme 5: Synthesis of Compound IX:

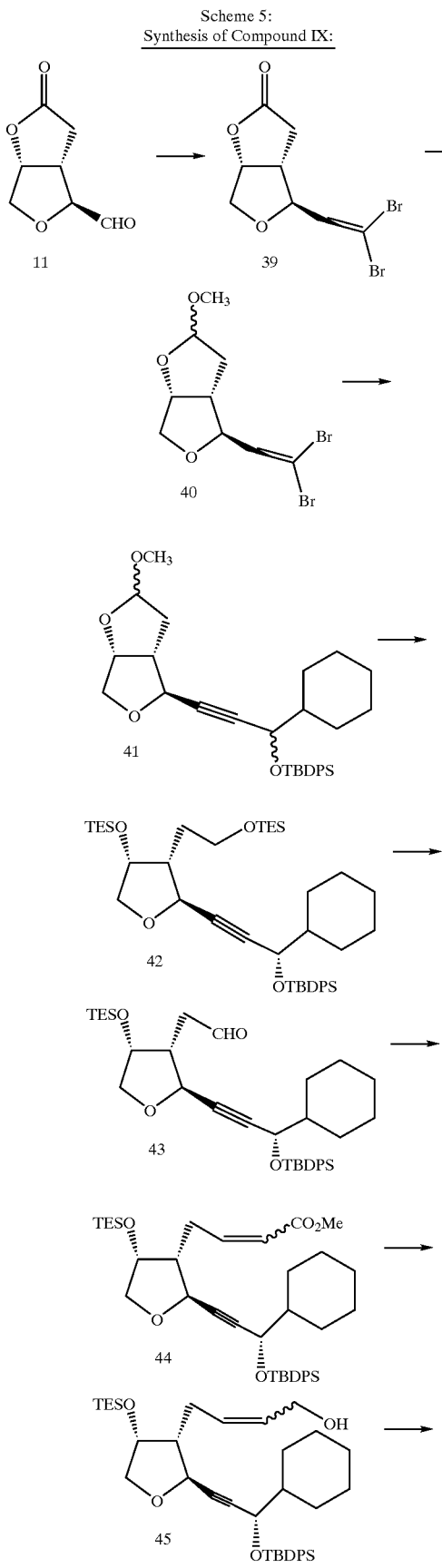

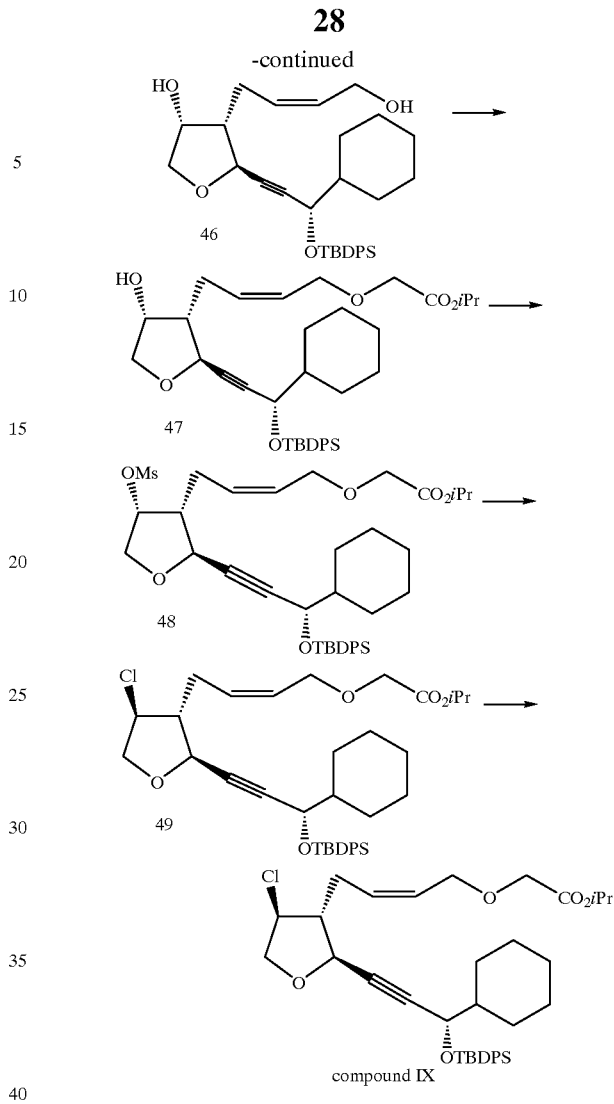

Isopropyl [2S(3S),3R(5Z),4S]-7-[Tetrahydro-4-Chloro-2-(3-Cyclohexyl-3-Hydroxy-1-Propynyl)-3-Furanyl]-3-Oxa-5-Heptenoate (IX)

The aldehyde 11 is treated with $CBr_4$ and triphenylphosphine to form the dibromoolefin 39. Lactone 39 is reduced to the lactol with diisobutylaluminum hydride (DIBAL-H) and this intermediate is reacted with trimethyl orthoformate in the presence of a catalytic amount of p-toluenesulfonic acid to afford the methyl glycoside 40. Treatment of compound 40 with n-BuLi followed by cyclohexanecarboxaldehyde yields the propargyl alcohol intermediate, which is reacted with tert-butyldiphenylsilyl chloride in the presence of base to afford the silyl ether 41. The methylglycoside moiety is removed by treatment of 41 with p-toluenesulfonic acid in refluxing THF/water, and the intermediate lactol is further reduced with DIBAL-H to the diol; treatment of the intermediate diol with chlorotriethylsilane (3 equivalents) under standard conditions, followed by separation of the diastereomers by column chromatography on silica affords the fully protected compound 42. Swern oxidation of 42 affords the aldehyde 43, which is homologated with bis(2,2,2-trifluoroethyl)(methoxycarbonylmethyl)phosphonate in the presence of KHMDS to give the diastereomeric mixture of crotonates 44. The ester 44 is reduced with DIBAL-H to the diastereomeric mixture of allylic alcohols 45 which is selectively deprotected (AcOH, $H_2O$, THF, room temperature), and the intermediate diol diastereomers are separated by column chromatography to afford the allylic alcohol 46. The diol 46 is alkylated with isopropyl bromoacetate under phase-transfer conditions (toluene, $H_2O$, NaOH, $(n\text{-Bu})_4NHSO_4$, 0° C.) to give the ester 47, which is reacted with methansulfonyl chloride in the presence of pyridine to afford the mesylate 48. Treatment of the mesylate 48 with LiCl in DMF at 80° C. gives the chlorinated compound 49 which when reacted with tetra-n-butylammonium fluoride affords compound IX.

The substituted tetrahydrofurans of the present invention may be formulated in various pharmaceutical compositions for administering to humans and other mammals as a treatment of glaucoma or ocular hypertension. As used herein, the term "pharmaceutically effective amount" refers to that amount of a compound of the present invention which lowers IOP when administered to a patient, especially a mammal. The preferred route of administration is topical. The compounds of the present invention can be administered as solutions, suspensions, or emulsions (dispersions) in an ophthalmically acceptable vehicle. As used herein, the term "ophthalmically acceptable vehicle" refers to any substance or combination of substances which are non-reactive with the compounds and suitable for administration to a patient. Solubilizers and stabilizers are deemed to be non-reactive. Preferred are aqueous vehicles suitable for topical application to the patient's eyes.

In forming compositions for topical administration, the compounds of the present invention are generally formulated as between about 0.00003 to about 0.5 percent by weight (wt %) solutions in water at a pH between about 4.5 to about 8.0, preferably between about 5.0 and about 7.5. The compounds are preferably formulated as between about 0.0005 to about 0.03 wt % and, most preferably, between about 0.001 and about 0.01 wt %. While the precise regimen is left to the discretion of the clinician, it is recommended that the resulting solution be topically applied by placing one drop in each eye one or two times a day.

Other ingredients which may be desirable to use in the ophthalmic preparations of the present invention include preservatives, co-solvents, and viscosity building agents.

Antimicrobial Preservatives:

Ophthalmic products are typically packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, Onamer M, or other agents known to those skilled in the art. Such preservatives are typically employed at a level between about 0.001% and about 1.0% by weight.

Co-Solvents:

Prostaglandins, and particularly ester derivatives, typically have limited solubility in water and therefore may require a surfactant or other appropriate co-solvent in the composition. Such co-solvents include: Polysorbate 20, 60 and 80; Pluronic F-68, F-84 and P-103; CREMOPHORE® EL (polyoxyl 35 castor oil); cyclodextrin; or other agents known to those skilled in the art. Such co-solvents are typically employed at a level between about 0.01% and about 2% by weight.

Viscosity Agents:

Viscosity greater than that of simple aqueous solutions may be desirable to increase ocular absorption of the active compound, to decrease variability in dispensing the formulations, to decrease physical separation of components of a suspension or emulsion of formulation and/or otherwise to improve the ophthalmic formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and other agents known to those skilled in the art. Such agents are typically employed at a level between about 0.01% and about 2% by weight.

Preferred formulations of substituted tetrahydrofurans of the present invention include the following Examples 6–8:

EXAMPLE 6

| Ingredient | Amount (wt %) |
|---|---|
| Compound VI | 0.01 |
| Monobasic sodium phosphate | 0.05 |
| Dibasic sodium phosphate (anhydrous) | 0.15 |
| Sodium chloride | 0.75 |
| Disodium EDTA (Edetate disodium) | 0.05 |
| Cremophor ® EL | 0.1 |
| Benzalkonium chloride | 0.01 |
| HCl and/or NaOH | q.s. pH 7.3–7.4 |
| Purified water | q.s. 100% |

EXAMPLE 7

| Ingredient | Amount (wt %) |
|---|---|
| Compound VII | 0.003 |
| Sodium acetate (trihydrate) | 0.07 |
| Mannitol | 4.3 |
| Disodium EDTA (Edetate disodium) | 0.1 |
| Cremophor ® EL | 0.5 |
| Benzalkonium chloride | 0.01 |
| HCl and/or NaOH | q.s. pH 5.0 |
| Purified water | q.s. 100% |

EXAMPLE 8

| Ingredient | Amount (wt %) |
|---|---|
| Compound VIII | 0.05 |
| Phosphate Buffered Saline | 1.0 |
| Hydroxypropyl-β-cyclodextrin | 4.0 |
| Purified water | q.s. 100% |

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A compound having the following formula:

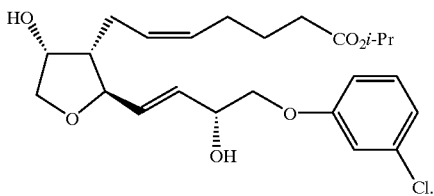

2. An ophthalmic composition for the treatment of glaucoma and ocular hypertension comprising the compound of claim 1 and an ophthalmically acceptable vehicle thereof.

3. A method of treating glaucoma and ocular hypertension in a patient, which comprises administering to the patient a pharmaceutically acceptable effective amount of the compound of claim 1.

4. The method of claim 3, wherein the compound is administered topically.

5. The method of claim 4, wherein the concentration of the compound is between about 0.0005 to about 0.03 weight.

6. The method of claim 5, wherein the concentration of the compound is between about 0.001 and about 0.01 weight percent.

* * * * *